US012653520B2

(12) United States Patent (10) Patent No.: US 12,653,520 B2

Rippe et al. (45) Date of Patent: *Jun. 16, 2026

---

(54) SYNDESMOSIS FIXATION ASSEMBLY

(71) Applicant: GLOBUS MEDICAL, INC., Audubon, PA (US)

(72) Inventors: Bradford H. Rippe, Media, PA (US); Kevin Gahman, Douglassville, PA (US); Peter Evans, Lafayette Hill, PA (US); James Gault, Philadelphia, PA (US); Zachary Shiner, Philadelphia, PA (US)

(73) Assignee: Globus Medical, Inc., Audubon, PA (US)

( * ) Notice: Subject to any disclaimer, the term of this patent is extended or adjusted under 35 U.S.C. 154(b) by 102 days.

This patent is subject to a terminal disclaimer.

(21) Appl. No.: 18/884,183

(22) Filed: Sep. 13, 2024

(65) Prior Publication Data

US 2025/0000505 A1 Jan. 2, 2025

Related U.S. Application Data

(60) Division of application No. 18/340,505, filed on Jun. 23, 2023, now Pat. No. 12,114,850, which is a (Continued)

(51) Int. Cl.
*A61B 17/04* (2006.01)
*A61F 2/42* (2006.01)

(52) U.S. Cl.
CPC ........ *A61B 17/0401* (2013.01); *A61F 2/4202* (2013.01); *A61B 2017/0414* (2013.01); *A61B 2017/044* (2013.01); *A61B 2017/0496* (2013.01)

(58) Field of Classification Search
CPC ........ A61B 17/0401; A61B 2017/0414; A61B 2017/044; A61B 2017/0496; A61F 2/4202
See application file for complete search history.

(56) References Cited

U.S. PATENT DOCUMENTS

| 254,473 | A | * | 3/1882 | Gates | ...................... F16G 11/00 403/33 |
| 1,105,105 | A | | 7/1914 | Sherman | |

(Continued)

FOREIGN PATENT DOCUMENTS

| CN | 201987653 U | 9/2011 |
| CN | 202313691 U | 7/2012 |

(Continued)

*Primary Examiner* — Phong Son H Dang

(57) ABSTRACT

Syndesmosis fixation assemblies, systems, and methods thereof. A syndesmosis fixation assembly includes a suture retaining portion having a plurality of suture openings formed therein and a suture securing portion rotatably connected to the suture retaining portion. The suture securing portion is movable between a first position wherein a suture is moveable within the suture retaining portion and a second position wherein the suture is frictionally secured within the suture retaining portion. A bone insertion portion has a distal bone insertion end adapted for insertion into a bone, a proximal bone insertion end connected to the suture retaining portion, and a central longitudinal axis extending between the distal bone insertion end and the proximal bone insertion end.

7 Claims, 16 Drawing Sheets

Related U.S. Application Data continuation of application No. 16/717,589, filed on Dec. 17, 2019, now Pat. No. 11,723,647.

(56) References Cited

U.S. PATENT DOCUMENTS

| | | | |
|---|---|---|---|
| 2,486,303 A | | 10/1949 | Longfellow |
| 2,907,978 A | * | 10/1959 | Bergan .................. H01R 4/363 |
| | | | 439/811 |
| 3,463,148 A | | 8/1969 | Treace |
| 3,695,259 A | | 10/1972 | Yost |
| 3,716,050 A | | 2/1973 | Johnston |
| 4,219,015 A | | 8/1980 | Steinemann |
| 4,493,317 A | | 1/1985 | Klaue |
| 4,524,765 A | | 6/1985 | de Zbikowski |
| 4,651,724 A | | 3/1987 | Berentey et al. |
| 4,683,878 A | | 8/1987 | Carter |
| 4,781,183 A | | 11/1988 | Casey et al. |
| 4,867,144 A | | 9/1989 | Karas et al. |
| 4,923,471 A | | 5/1990 | Morgan |
| 4,966,599 A | | 10/1990 | Pollock |
| 5,002,544 A | | 3/1991 | Klaue et al. |
| 5,041,114 A | | 8/1991 | Chapman et al. |
| 5,151,103 A | | 9/1992 | Tepic et al. |
| 5,259,398 A | | 11/1993 | Vrespa |
| 5,364,399 A | | 11/1994 | Lowery et al. |
| 5,372,598 A | | 12/1994 | Luhr et al. |
| 5,423,826 A | | 6/1995 | Coates et al. |
| 5,468,242 A | | 11/1995 | Reisberg |
| D365,634 S | | 12/1995 | Morgan |
| 5,489,305 A | | 2/1996 | Morgan |
| 5,527,311 A | | 6/1996 | Procter et al. |
| 5,578,036 A | | 11/1996 | Stone et al. |
| 5,601,553 A | | 2/1997 | Trebing et al. |
| 5,676,667 A | | 10/1997 | Hausman |
| 5,690,631 A | | 11/1997 | Duncan et al. |
| 5,709,686 A | | 1/1998 | Talos et al. |
| 5,709,687 A | | 1/1998 | Pennig |
| 5,718,704 A | | 2/1998 | Medoff |
| 5,718,705 A | | 2/1998 | Sammarco |
| 5,746,742 A | | 5/1998 | Runciman et al. |
| 5,766,175 A | | 6/1998 | Martinotti |
| 5,766,176 A | | 6/1998 | Duncan |
| 5,779,706 A | | 7/1998 | Tschakaloff |
| 5,785,712 A | | 7/1998 | Runciman et al. |
| 5,797,914 A | | 8/1998 | Leibinger |
| 5,814,048 A | | 9/1998 | Morgan |
| 5,925,048 A | | 7/1999 | Ahmad et al. |
| 5,938,664 A | | 8/1999 | Winquist et al. |
| 5,957,953 A | * | 9/1999 | DiPoto .............. A61B 17/0401 |
| | | | 606/313 |
| 5,961,519 A | | 10/1999 | Bruce et al. |
| 5,980,540 A | | 11/1999 | Bruce |
| 6,001,099 A | | 12/1999 | Huebner |
| 6,071,291 A | | 6/2000 | Forst et al. |
| 6,093,201 A | | 7/2000 | Cooper et al. |
| 6,096,040 A | | 8/2000 | Esser |
| 6,107,718 A | | 8/2000 | Schustek et al. |
| 6,152,927 A | | 11/2000 | Farris et al. |
| 6,206,881 B1 | | 3/2001 | Frigg et al. |
| 6,283,969 B1 | | 9/2001 | Grusin et al. |
| 6,309,393 B1 | | 10/2001 | Tepic et al. |
| 6,322,562 B1 | | 11/2001 | Wolter |
| 6,364,882 B1 | | 4/2002 | Orbay |
| D458,683 S | | 6/2002 | Bryant et al. |
| D458,684 S | | 6/2002 | Bryant et al. |
| 6,533,786 B1 | | 3/2003 | Needham et al. |
| D479,331 S | | 9/2003 | Pike et al. |
| 6,623,486 B1 | | 9/2003 | Weaver et al. |
| 6,669,700 B1 | | 12/2003 | Farris et al. |
| 6,669,701 B2 | | 12/2003 | Steiner et al. |
| 6,712,820 B2 | | 3/2004 | Orbay |
| 6,719,759 B2 | | 4/2004 | Wagner et al. |
| 6,730,091 B1 | | 5/2004 | Pfefferle et al. |
| 6,866,665 B2 | | 3/2005 | Orbay |

| | | | |
|---|---|---|---|
| 6,932,834 B2 | * | 8/2005 | Lizardi ................. A61F 2/0811 |
| | | | 606/228 |
| 6,955,677 B2 | | 10/2005 | Dahners |
| 6,974,461 B1 | | 12/2005 | Wolter |
| 7,001,387 B2 | | 2/2006 | Farris et al. |
| 7,063,701 B2 | | 6/2006 | Michelson |
| 7,090,676 B2 | | 8/2006 | Huebner et al. |
| 7,128,744 B2 | | 10/2006 | Weaver et al. |
| 7,137,987 B2 | | 11/2006 | Patterson et al. |
| 7,153,309 B2 | | 12/2006 | Huebner et al. |
| 7,179,260 B2 | | 2/2007 | Gerlach et al. |
| 7,250,053 B2 | | 7/2007 | Orbay |
| 7,294,130 B2 | | 11/2007 | Orbay |
| 7,322,983 B2 | | 1/2008 | Harris |
| 7,341,589 B2 | | 3/2008 | Weaver et al. |
| 7,344,538 B2 | | 3/2008 | Myerson et al. |
| 7,354,441 B2 | | 4/2008 | Frigg |
| 7,604,657 B2 | | 10/2009 | Orbay et al. |
| 7,632,277 B2 | | 12/2009 | Woll et al. |
| 7,635,381 B2 | | 12/2009 | Orbay |
| 7,637,928 B2 | | 12/2009 | Fernandez |
| 7,655,029 B2 | | 2/2010 | Niedernberger et al. |
| 7,655,047 B2 | | 2/2010 | Swords |
| 7,695,472 B2 | | 4/2010 | Young |
| 7,717,946 B2 | | 5/2010 | Oepen et al. |
| 7,722,653 B2 | | 5/2010 | Young et al. |
| 7,740,648 B2 | | 6/2010 | Young et al. |
| D622,853 S | | 8/2010 | Raven, III |
| 7,771,457 B2 | | 8/2010 | Kay et al. |
| 7,776,076 B2 | | 8/2010 | Grady, Jr. et al. |
| 7,857,838 B2 | | 12/2010 | Orbay |
| 7,867,260 B2 | | 1/2011 | Meyer et al. |
| 7,867,261 B2 | | 1/2011 | Sixto, Jr. et al. |
| 7,875,062 B2 | | 1/2011 | Lindemann et al. |
| 7,905,910 B2 | | 3/2011 | Gerlach et al. |
| 7,909,858 B2 | | 3/2011 | Gerlach et al. |
| 7,951,178 B2 | | 5/2011 | Jensen |
| 7,951,179 B2 | | 5/2011 | Matityahu |
| 7,976,570 B2 | | 7/2011 | Wagner et al. |
| D643,121 S | | 8/2011 | Millford et al. |
| D646,785 S | | 10/2011 | Milford |
| 8,043,297 B2 | | 10/2011 | Grady, Jr. et al. |
| 8,057,520 B2 | | 11/2011 | Ducharme et al. |
| 8,062,296 B2 | | 11/2011 | Orbay et al. |
| 8,100,953 B2 | | 1/2012 | White et al. |
| 8,105,367 B2 | | 1/2012 | Austin et al. |
| 8,114,081 B2 | | 2/2012 | Kohut et al. |
| 8,118,846 B2 | | 2/2012 | Leither et al. |
| 8,118,848 B2 | | 2/2012 | Ducharme et al. |
| 8,162,950 B2 | | 4/2012 | Digeser et al. |
| 8,162,978 B2 | * | 4/2012 | Lombardo ............ A61F 2/0805 |
| | | | 606/232 |
| 8,167,918 B2 | | 5/2012 | Strnad et al. |
| 8,177,820 B2 | | 5/2012 | Anapliotis et al. |
| 8,246,661 B2 | | 8/2012 | Beutter et al. |
| 8,252,032 B2 | | 8/2012 | White et al. |
| 8,257,403 B2 | | 9/2012 | Den Hartog et al. |
| 8,257,405 B2 | | 9/2012 | Haidukewych et al. |
| 8,257,406 B2 | | 9/2012 | Kay et al. |
| 8,262,707 B2 | | 9/2012 | Huebner et al. |
| 8,267,972 B1 | | 9/2012 | Gehlert |
| 8,317,842 B2 | | 11/2012 | Graham et al. |
| 8,323,321 B2 | | 12/2012 | Gradl |
| 8,337,535 B2 | | 12/2012 | White et al. |
| 8,343,155 B2 | | 1/2013 | Fisher et al. |
| 8,382,807 B2 | | 2/2013 | Austin et al. |
| 8,394,098 B2 | | 3/2013 | Orbay et al. |
| 8,394,130 B2 | | 3/2013 | Orbay et al. |
| 8,398,685 B2 | | 3/2013 | McGarity et al. |
| 8,403,966 B2 | | 3/2013 | Ralph et al. |
| 8,419,775 B2 | | 4/2013 | Orbay et al. |
| 8,435,272 B2 | | 5/2013 | Dougherty et al. |
| 8,439,918 B2 | | 5/2013 | Gelfand |
| 8,444,679 B2 | | 5/2013 | Ralph et al. |
| 8,491,593 B2 | | 7/2013 | Prien et al. |
| 8,506,608 B2 | | 8/2013 | Cerynik et al. |
| 8,512,384 B2 | | 8/2013 | Beutter et al. |
| 8,512,385 B2 | | 8/2013 | White et al. |
| 8,518,090 B2 | | 8/2013 | Huebner et al. |

(56)        References Cited

U.S. PATENT DOCUMENTS

| | | | |
|---|---|---|---|
| 8,523,862 B2 | 9/2013 | Murashko, Jr. | |
| 8,523,919 B2 | 9/2013 | Huebner et al. | |
| 8,523,921 B2 | 9/2013 | Horan et al. | |
| 8,540,755 B2 | 9/2013 | Whitmore | |
| 8,545,535 B2 * | 10/2013 | Hirotsuka .......... A61B 17/0401 |
| | | | 606/232 |
| 8,551,095 B2 | 10/2013 | Fritzinger et al. | |
| 8,551,143 B2 | 10/2013 | Norris et al. | |
| 8,568,462 B2 | 10/2013 | Sixto, Jr. et al. | |
| 8,574,268 B2 | 11/2013 | Chan et al. | |
| 8,597,334 B2 | 12/2013 | Mocanu | |
| 8,603,147 B2 | 12/2013 | Sixto, Jr. et al. | |
| 8,617,224 B2 | 12/2013 | Kozak et al. | |
| 8,632,574 B2 | 1/2014 | Kortenbach et al. | |
| 8,641,741 B2 | 2/2014 | Murashko, Jr. | |
| 8,641,744 B2 | 2/2014 | Weaver et al. | |
| 8,663,224 B2 | 3/2014 | Overes et al. | |
| 8,728,082 B2 | 5/2014 | Fritzinger et al. | |
| 8,728,126 B2 | 5/2014 | Steffen | |
| 8,740,905 B2 | 6/2014 | Price et al. | |
| 8,747,442 B2 | 6/2014 | Orbay et al. | |
| 8,764,751 B2 | 7/2014 | Orbay et al. | |
| 8,764,808 B2 | 7/2014 | Gonzalez-Hernandez | |
| 8,777,998 B2 | 7/2014 | Daniels et al. | |
| 8,790,376 B2 | 7/2014 | Fritzinger et al. | |
| 8,790,377 B2 | 7/2014 | Ralph et al. | |
| 8,808,333 B2 | 8/2014 | Kuster et al. | |
| 8,808,334 B2 | 8/2014 | Strnad et al. | |
| 8,834,532 B2 | 9/2014 | Velikov et al. | |
| 8,834,537 B2 | 9/2014 | Castanada et al. | |
| 8,852,246 B2 | 10/2014 | Hansson | |
| 8,852,249 B2 | 10/2014 | Ahrens et al. | |
| 8,864,802 B2 | 10/2014 | Schwager et al. | |
| 8,870,931 B2 | 10/2014 | Dahners et al. | |
| 8,888,825 B2 | 11/2014 | Batsch et al. | |
| 8,906,076 B2 | 12/2014 | Mocanu et al. | |
| 8,911,482 B2 | 12/2014 | Lee et al. | |
| 8,926,675 B2 | 1/2015 | Leung et al. | |
| 8,940,026 B2 | 1/2015 | Hilse et al. | |
| 8,940,028 B2 | 1/2015 | Austin et al. | |
| 8,940,029 B2 | 1/2015 | Leung et al. | |
| 8,951,291 B2 | 2/2015 | Impellizzeri | |
| 8,968,368 B2 | 3/2015 | Tepic | |
| 9,011,457 B2 | 4/2015 | Grady, Jr. et al. | |
| 9,023,052 B2 | 5/2015 | Lietz et al. | |
| 9,050,151 B2 | 6/2015 | Schilter | |
| 9,072,555 B2 | 7/2015 | Michel | |
| 9,072,557 B2 | 7/2015 | Fierlbeck et al. | |
| 9,107,678 B2 | 8/2015 | Murner et al. | |
| 9,107,711 B2 | 8/2015 | Hainard | |
| 9,107,713 B2 | 8/2015 | Horan et al. | |
| 9,107,718 B2 | 8/2015 | Isch | |
| 9,113,970 B2 | 8/2015 | Lewis et al. | |
| 9,149,310 B2 | 10/2015 | Fritzinger et al. | |
| 9,161,791 B2 | 10/2015 | Frigg | |
| 9,161,795 B2 | 10/2015 | Chasbrummel et al. | |
| 9,168,075 B2 | 10/2015 | Dell'Oca | |
| 9,179,950 B2 | 11/2015 | Zajac et al. | |
| 9,179,956 B2 | 11/2015 | Cerynik et al. | |
| 9,180,020 B2 | 11/2015 | Gause et al. | |
| 9,211,151 B2 | 12/2015 | Weaver et al. | |
| 9,259,217 B2 | 2/2016 | Fritzinger et al. | |
| 9,259,255 B2 | 2/2016 | Lewis et al. | |
| 9,271,769 B2 | 3/2016 | Batsch et al. | |
| 9,283,010 B2 | 3/2016 | Medoff et al. | |
| 9,295,506 B2 | 3/2016 | Raven, III et al. | |
| 9,314,284 B2 | 4/2016 | Chan et al. | |
| 9,320,554 B2 | 4/2016 | Greenberg et al. | |
| 9,322,562 B2 | 4/2016 | Takayama et al. | |
| 9,370,388 B2 | 6/2016 | Globerman et al. | |
| D765,851 S | 9/2016 | Early et al. | |
| 9,433,407 B2 | 9/2016 | Fritzinger et al. | |
| 9,433,452 B2 | 9/2016 | Weiner et al. | |
| 9,468,479 B2 | 10/2016 | Marotta et al. | |
| 9,480,512 B2 | 11/2016 | Orbay | |
| 9,486,262 B2 | 11/2016 | Andermahr et al. | |
| 9,492,213 B2 | 11/2016 | Orbay | |
| 9,510,878 B2 | 12/2016 | Nanavati et al. | |
| 9,510,880 B2 | 12/2016 | Terrill et al. | |
| 9,526,543 B2 | 12/2016 | Castaneda et al. | |
| 9,545,277 B2 | 1/2017 | Wolf et al. | |
| 9,549,819 B1 | 1/2017 | Bravo et al. | |
| 9,566,097 B2 | 2/2017 | Fierlbeck et al. | |
| 9,579,133 B2 | 2/2017 | Guthlein | |
| 9,622,737 B2 * | 4/2017 | Gerber ............... A61B 17/0401 |
| 9,622,799 B2 | 4/2017 | Orbay et al. | |
| 9,636,157 B2 | 5/2017 | Medoff | |
| 9,649,141 B2 | 5/2017 | Raven, III et al. | |
| 9,668,794 B2 | 6/2017 | Kuster et al. | |
| 9,801,670 B2 | 10/2017 | Hashmi et al. | |
| 9,814,504 B2 | 11/2017 | Ducharme et al. | |
| 9,980,718 B2 * | 5/2018 | Housman .......... A61B 17/0401 |
| 10,111,652 B2 * | 10/2018 | Patel .................. A61B 17/0401 |
| 10,595,849 B2 * | 3/2020 | Kaplan .............. A61B 17/0487 |
| 10,945,830 B2 * | 3/2021 | Dacosta ............. A61B 17/8625 |
| 2002/0045901 A1 | 4/2002 | Wagner et al. | |
| 2002/0147463 A1 * | 10/2002 | Martinek ........... A61B 17/0401 |
| | | | 606/232 |
| 2004/0097937 A1 | 5/2004 | Pike et al. | |
| 2005/0107796 A1 | 5/2005 | Gerlach et al. | |
| 2005/0131413 A1 | 6/2005 | O'Driscoll et al. | |
| 2005/0187551 A1 | 8/2005 | Orbay et al. | |
| 2006/0149265 A1 | 7/2006 | James et al. | |
| 2006/0241607 A1 | 10/2006 | Myerson et al. | |
| 2007/0173840 A1 | 7/2007 | Huebner | |
| 2007/0270849 A1 | 11/2007 | Orbay et al. | |
| 2007/0288022 A1 | 12/2007 | Lutz | |
| 2008/0021477 A1 | 1/2008 | Strnad et al. | |
| 2008/0234749 A1 | 9/2008 | Forstein | |
| 2008/0275510 A1 | 11/2008 | Schonhardt et al. | |
| 2009/0024172 A1 | 1/2009 | Pizzicara | |
| 2009/0024173 A1 | 1/2009 | Reis, Jr. | |
| 2009/0112270 A1 * | 4/2009 | Lunn .................. A61B 17/0401 |
| | | | 606/301 |
| 2009/0118773 A1 | 5/2009 | James et al. | |
| 2009/0157124 A1 * | 6/2009 | Ferragamo ......... A61B 17/0642 |
| | | | 606/301 |
| 2009/0198285 A1 | 8/2009 | Raven, III | |
| 2009/0228010 A1 | 9/2009 | Gonzalez-Hernandez et al. | |
| 2009/0228047 A1 | 9/2009 | Derouet et al. | |
| 2009/0248084 A1 | 10/2009 | Hintermann | |
| 2009/0281543 A1 | 11/2009 | Orbay et al. | |
| 2009/0299369 A1 | 12/2009 | Orbay et al. | |
| 2009/0312760 A1 | 12/2009 | Forstein et al. | |
| 2010/0057086 A1 | 3/2010 | Price et al. | |
| 2010/0114097 A1 | 5/2010 | Siravo et al. | |
| 2010/0121326 A1 | 5/2010 | Woll et al. | |
| 2010/0274247 A1 | 10/2010 | Grady, Jr. et al. | |
| 2010/0318125 A1 * | 12/2010 | Gerber ............... A61B 17/0401 |
| | | | 606/232 |
| 2011/0106086 A1 | 5/2011 | Laird | |
| 2011/0112576 A1 * | 5/2011 | Nguyen ............. A61B 17/0401 |
| | | | 606/232 |
| 2011/0218580 A1 | 9/2011 | Schwager et al. | |
| 2012/0010667 A1 | 1/2012 | Eglseder | |
| 2012/0059424 A1 | 3/2012 | Epperly et al. | |
| 2012/0203227 A1 | 8/2012 | Martin | |
| 2012/0232599 A1 | 9/2012 | Schoenly et al. | |
| 2012/0323284 A1 | 12/2012 | Baker et al. | |
| 2013/0006302 A1 * | 1/2013 | Paulk .................... A61F 2/0811 |
| | | | 606/232 |
| 2013/0018426 A1 | 1/2013 | Tsai et al. | |
| 2013/0046347 A1 | 2/2013 | Cheng et al. | |
| 2013/0060291 A1 | 3/2013 | Petersheim | |
| 2013/0123841 A1 | 5/2013 | Lyon | |
| 2013/0138156 A1 | 5/2013 | Derouet | |
| 2013/0150902 A1 | 6/2013 | Leite | |
| 2013/0165981 A1 | 6/2013 | Clasbrummet et al. | |
| 2013/0211463 A1 | 8/2013 | Mizuno et al. | |
| 2013/0289630 A1 | 10/2013 | Fritzinger | |
| 2014/0005728 A1 | 1/2014 | Koay et al. | |
| 2014/0018862 A1 | 1/2014 | Koay et al. | |
| 2014/0031879 A1 | 1/2014 | Sixto, Jr. et al. | |
| 2014/0066998 A1 | 3/2014 | Martin | |

(56)     References Cited

U.S. PATENT DOCUMENTS

| 2014/0094856 A1 | 4/2014 | Sinha |
| 2014/0121710 A1 | 5/2014 | Weaver et al. |
| 2014/0180345 A1 | 6/2014 | Chan et al. |
| 2014/0277178 A1 | 9/2014 | O'Kane et al. |
| 2014/0277181 A1 | 9/2014 | Garlock |
| 2014/0316473 A1 | 10/2014 | Pfeffer et al. |
| 2014/0330320 A1 | 11/2014 | Wolter |
| 2014/0378975 A1 | 12/2014 | Castaneda et al. |
| 2015/0051650 A1 | 2/2015 | Verstreken et al. |
| 2015/0051651 A1 | 2/2015 | Terrill et al. |
| 2015/0073486 A1 | 3/2015 | Marotta et al. |
| 2015/0105829 A1 | 4/2015 | Laird |
| 2015/0112355 A1 | 4/2015 | Dahners et al. |
| 2015/0134011 A1 | 5/2015 | Medoff |
| 2015/0142065 A1 | 5/2015 | Schonhardt et al. |
| 2015/0190185 A1 | 7/2015 | Koay et al. |
| 2015/0209091 A1 | 7/2015 | Sixto, Jr. et al. |
| 2015/0216571 A1 | 8/2015 | Impellizzeri |
| 2015/0223852 A1 | 8/2015 | Lietz et al. |
| 2015/0272638 A1 | 10/2015 | Langford |
| 2015/0282851 A1 | 10/2015 | Michel |
| 2015/0313653 A1 | 11/2015 | Ponce et al. |
| 2015/0313654 A1 | 11/2015 | Horan et al. |
| 2015/0327898 A1 | 11/2015 | Martin |
| 2015/0351816 A1 | 12/2015 | Lewis et al. |
| 2015/0374421 A1 | 12/2015 | Rocci et al. |
| 2016/0022336 A1 | 1/2016 | Bateman |
| 2016/0030035 A1 | 2/2016 | Zajac et al. |
| 2016/0045237 A1 | 2/2016 | Cerynik et al. |
| 2016/0045238 A1 | 2/2016 | Bohay et al. |
| 2016/0074081 A1 | 3/2016 | Weaver et al. |
| 2016/0166297 A1 | 6/2016 | Mighell et al. |
| 2016/0166298 A1 | 6/2016 | Mighell et al. |
| 2016/0183990 A1 | 6/2016 | Koizumi et al. |
| 2016/0262814 A1 | 9/2016 | Wainscott |
| 2016/0278828 A1 | 9/2016 | Ragghianti |
| 2016/0310183 A1 | 10/2016 | Shah et al. |
| 2016/0310185 A1 | 10/2016 | Sixto et al. |
| 2016/0324552 A1 | 11/2016 | Baker et al. |
| 2016/0354122 A1 | 12/2016 | Montello et al. |
| 2017/0035478 A1 | 2/2017 | Andermahr et al. |
| 2017/0042592 A1 | 2/2017 | Kim |
| 2017/0042596 A9 | 2/2017 | Mighell et al. |
| 2017/0049493 A1 | 2/2017 | Gauneau et al. |
| 2017/0065312 A1 | 3/2017 | Lauf et al. |
| 2017/0105775 A1 | 4/2017 | Ricker et al. |
| 2017/0215931 A1 | 8/2017 | Cremer et al. |
| 2019/0261973 A1* | 8/2019 | Kubiak ............... A61B 17/0401 |
| 2019/0336190 A1* | 11/2019 | Allard ................. A61B 17/683 |
| 2020/0245997 A1* | 8/2020 | Balboa ............... A61B 17/0401 |
| 2021/0177394 A1* | 6/2021 | Rippe ................ A61B 17/0401 |
| 2024/0164770 A1* | 5/2024 | Chao ..................... A61F 2/0811 |

FOREIGN PATENT DOCUMENTS

| CN | 202821574 U | 3/2013 |
| CN | 202821575 U | 3/2013 |
| CN | 203506858 U | 4/2014 |
| CN | 203815563 U | 9/2014 |
| CN | 105982727 A | 10/2016 |
| FR | 2846870 A1 | 5/2004 |
| FR | 2928259 A1 | 9/2009 |
| JP | 2003210478 A | 7/2003 |
| TW | 201316942 A | 5/2013 |
| WO | 2016079504 A1 | 5/2016 |

* cited by examiner

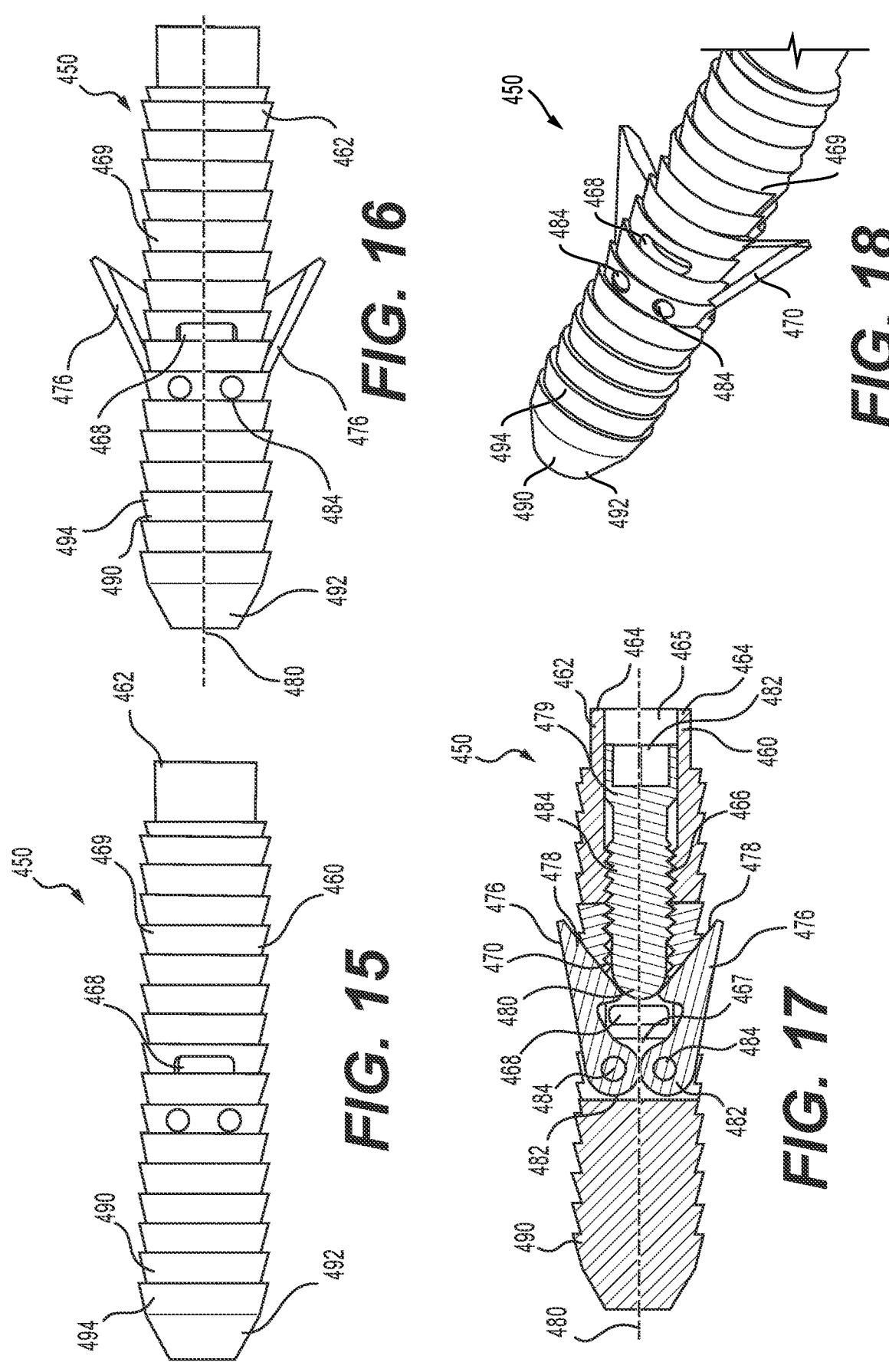

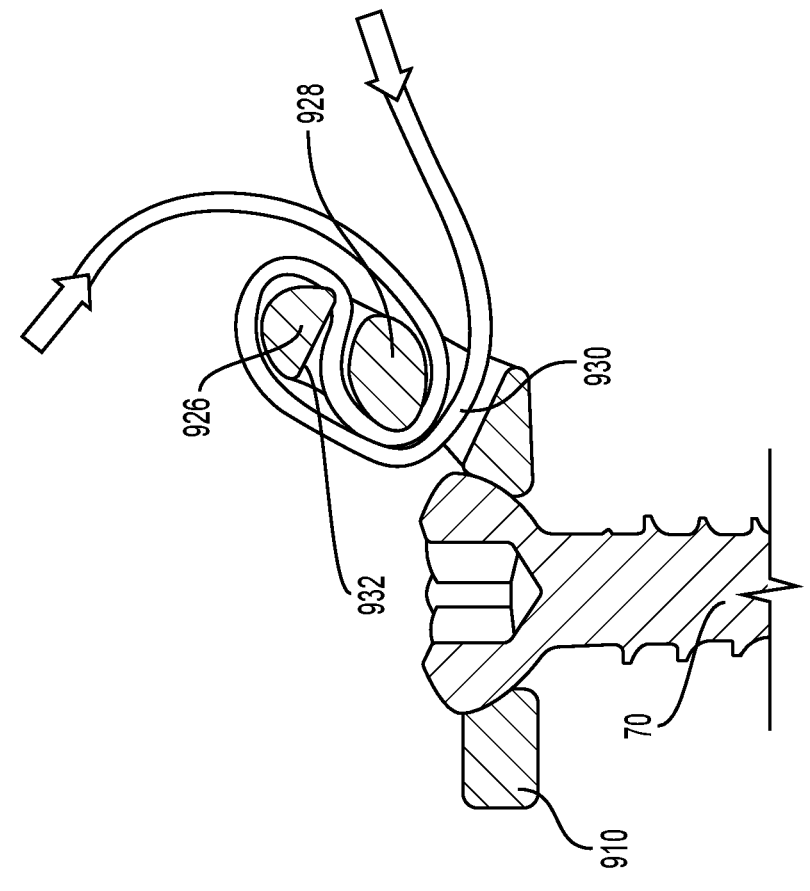
*FIG. 24*
*FIG. 23*

SYNDESMOSIS FIXATION ASSEMBLY

CROSS-REFERENCE TO RELATED APPLICATIONS

The present application is a divisional of U.S. patent application Ser. No. 18/340,505, filed on Jun. 23, 2023 (published as U.S. Pat. Pub. No. 2023-0389917), which is a continuation of U.S. patent application Ser. No. 16/717,589, filed on Dec. 17, 2019 (now U.S. Pat. No. 11,723,647), the entire contents of each of which are hereby incorporated by reference in their entirety.

FIELD

The present device relates to constructs that are used in the fixation of syndesmosis disruptions.

BACKGROUND

A present method for syndesmotic ankle fixation requires screws or suture button systems. Both types of these fixation devices are inserted through the fibula and into the syndesmosis. The cross section of the fibula is relatively small, particularly at the syndesmosis, which can result in the clinician having a difficult time inserting the screw or suture button system through the fibula.

Accordingly, there exists a need for a syndesmosis fixation system that does not extend through the fibula.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

According to one embodiment, a syndesmosis fixation assembly may include a plurality of implantable devices configured to aid in anatomic reduction.

In one embodiment, the syndesmosis fixation assembly may include a suture retaining portion having a plurality of suture openings formed therein and a suture securing portion rotatably connected to the suture retaining portion. The suture securing portion is movable between a first position wherein a suture is moveable within the suture retaining portion and a second position wherein the suture is frictionally secured within the suture retaining portion. A bone insertion portion has a distal bone insertion end adapted for insertion into a bone, a proximal bone insertion end connected to the suture retaining portion, and a central longitudinal axis extending between the distal bone insertion end and the proximal bone insertion end.

In an alternative embodiment, the syndesmosis fixation assembly includes a suture retaining portion having a plurality of suture openings formed therein and a suture extending through each of the plurality of suture openings. A suture securing portion is connected to the suture retaining portion. The suture securing portion is movable between a first position wherein the suture is moveable within the suture retaining portion and a second position wherein the suture is frictionally secured within the suture retaining portion. A bone insertion portion has a distal bone insertion end adapted for insertion into a bone and a proximal bone insertion end connected to the suture retaining portion.

In still another alternative embodiment, the syndesmosis fixation assembly comprises a suture retaining portion and a suture securing portion adapted to move from a first position wherein a suture in the suture retaining portion is moveable with respect to the suture retaining portion and a second position wherein the suture is fixed with respect to the suture retaining portion. A bone insertion portion has a distal portion adapted for insertion into a bone and a proximal portion connected to the suture retaining portion.

BRIEF DESCRIPTION OF THE DRAWINGS

Other aspects, features, and advantages of the present device will become more fully apparent from the following detailed description, the appended claims, and the accompanying drawings in which like reference numerals identify similar or identical elements.

FIG. 15 is a side elevational view of a fixation assembly according to an alternative exemplary embodiment;

FIG. 16 is a side elevational view of the assembly of FIG. 15 with anchor legs in a deployed position;

FIG. 17 is a sectional view of the assembly of FIG. 15 with the anchor legs in the deployed position;

FIG. 18 is a perspective view of the assembly of FIG. 15 with the anchors deployed;

FIG. 23 is a perspective view of a washer with a buckle used with the assembly of FIG. 22;

FIG. 24 is a sectional view of the assembly of FIG. 22;

DETAILED DESCRIPTION

Figure 2:
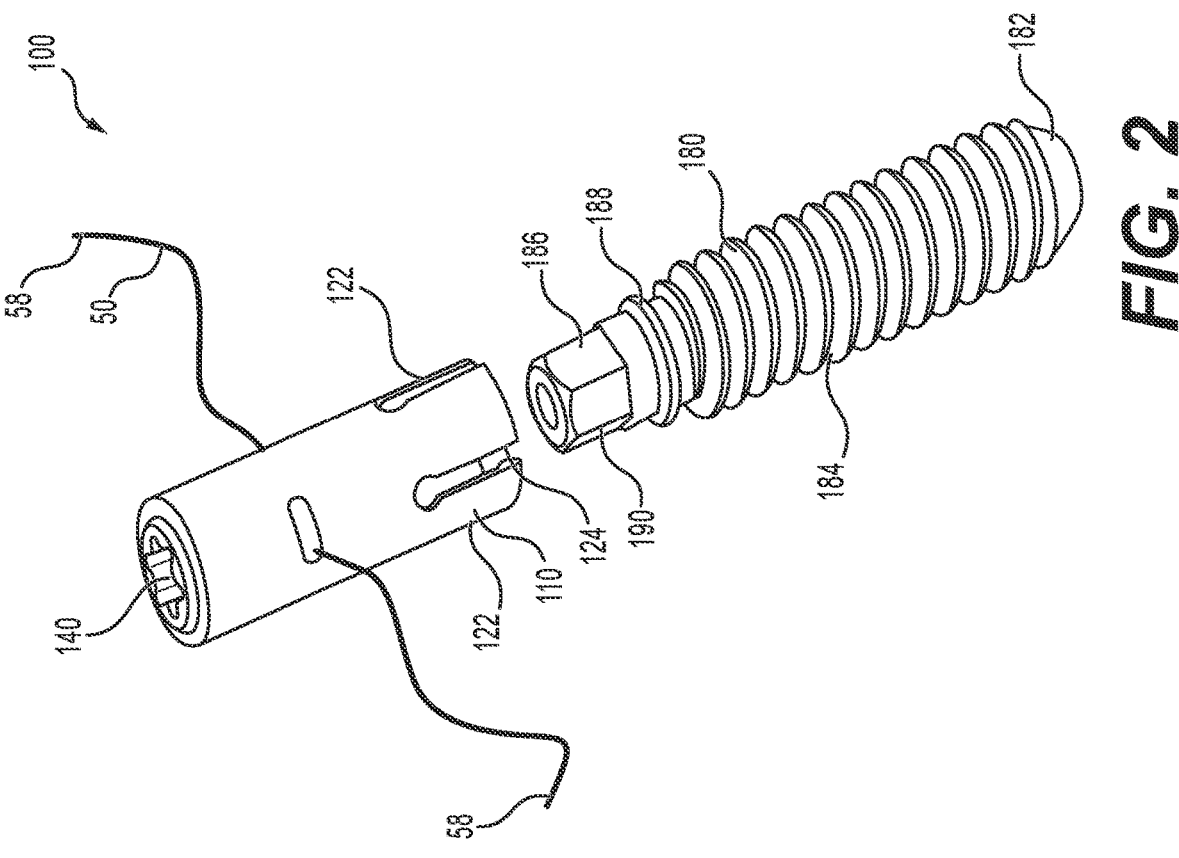
FIG. 2 is an exploded view of a fixation assembly according to an exemplary embodiment.

In the drawings, like numerals indicate like elements throughout. Certain terminology is used herein for convenience only and is not to be taken as a limitation on the present device. The terminology includes the words specifically mentioned, derivatives thereof and words of similar import. As used herein, the term "proximal" is intended to mean a direction closer to a clinician implanting the inventive devices and the term "distal" is intended to mean a direction farther from the clinician.

The embodiments illustrated below are not intended to be exhaustive or to limit the device to the precise form disclosed. These embodiments are chosen and described to best explain the principle of the device and its application and practical use and to enable others skilled in the art to best utilize the device.

Reference herein to "one embodiment" or "an embodiment" means that a particular feature, structure, or characteristic described in connection with the embodiment can be included in at least one embodiment of the device. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present device.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Also for purposes of this description, the terms "couple," "coupling," "coupled," "connect," "connecting," or "connected" refer to any manner known in the art or later developed of joining or connecting two or more elements directly or indirectly to one another, and the interposition of one or more additional elements is contemplated, although not required. Conversely, the terms "directly coupled," "directly connected," etc., imply the absence of such additional elements.

Figure 1:
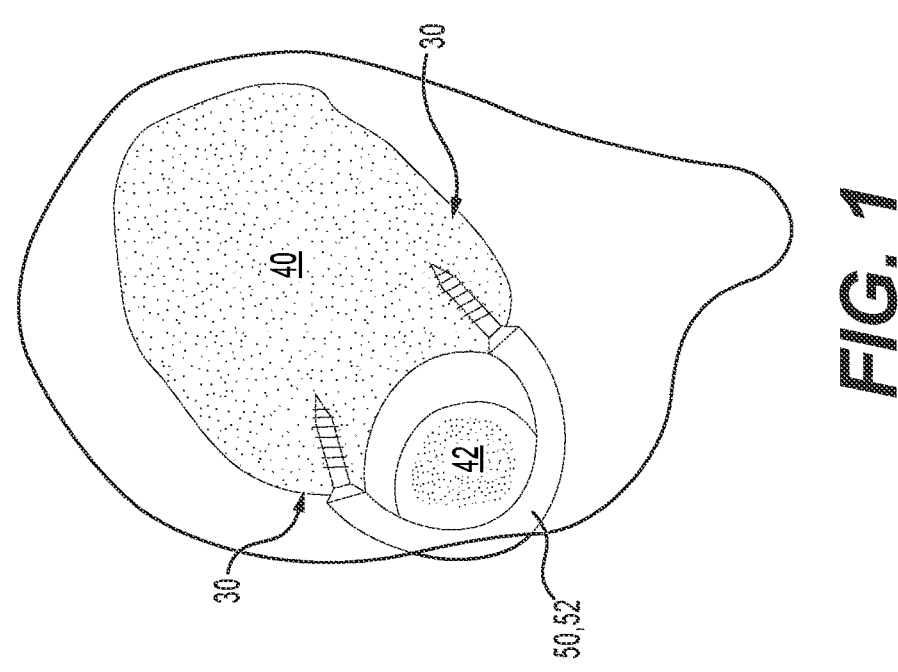
FIG. 1 is a sectional view showing an exemplary method of reducing a syndesmosis according to the exemplary embodiments.

The present disclosure provides embodiments of fixation device assemblies that can be used in syndesmosis fixation. The devices and assemblies described herein can be attached to a tibia 40 in two locations, with a suture 50 or suture tape connected to each device and wrapped around a fibula 42 to stabilize the syndesmosis. A simplified illustration of fixation device assemblies described herein is shown in FIG. 1, using generic screws 30 implanted into a tibia 40 on either side of a fibula 42, with a suture 50 or suture tape 52 connected to screws 30 and wrapped over fibula 42 to draw fibula 42 closer to tibia 40 and reduce the syndesmosis.

Figures 3, 4:
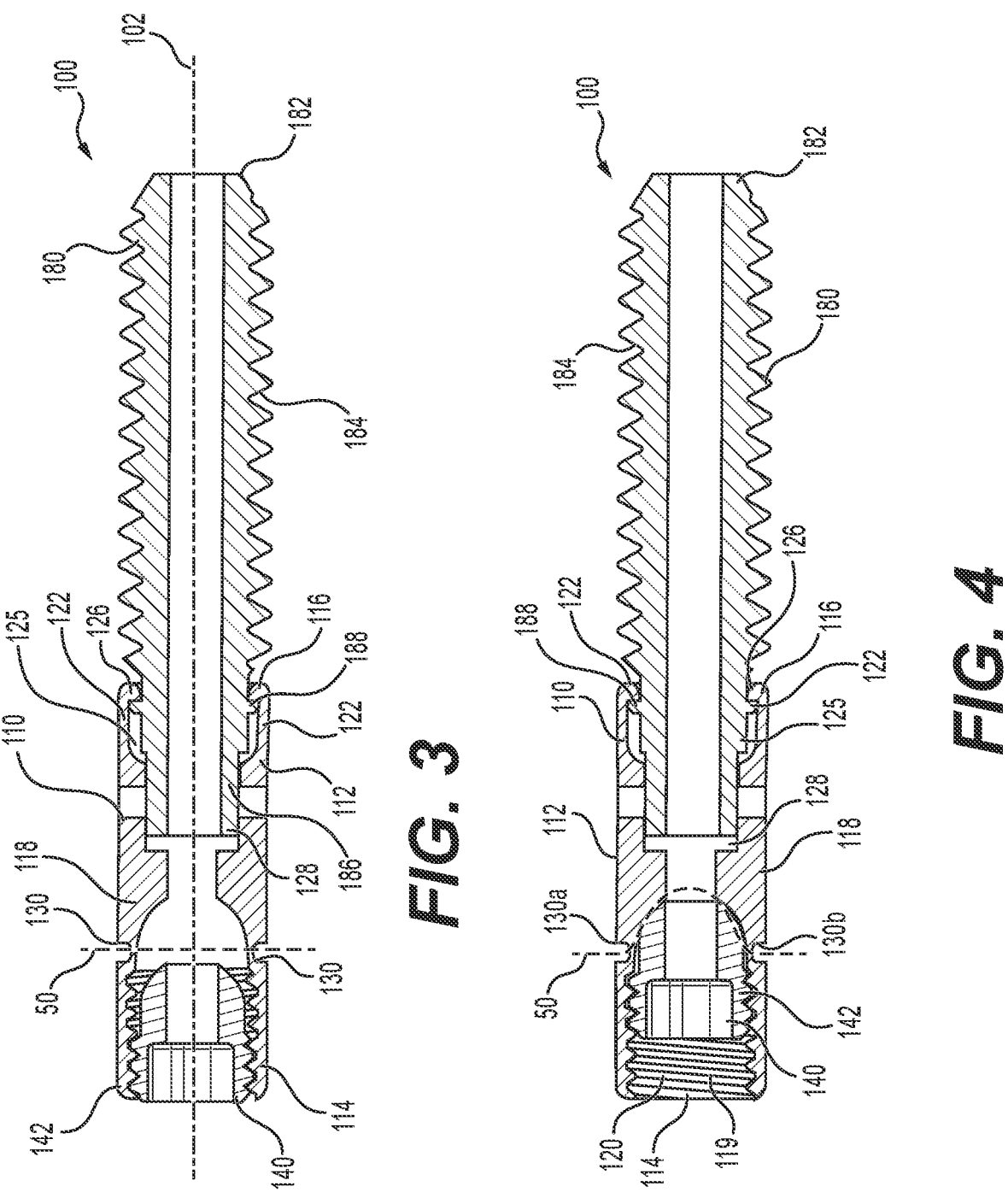
FIG. 3 is a sectional view of the assembly of FIG. 2 in a suture release position.
FIG. 4 is a sectional view of the assembly of FIG. 2 in a suture restraining position.

Referring to FIGS. 2-4, a syndesmosis fixation assembly 100 ("assembly 100") according to a first exemplary embodiment is shown. Assembly 100 includes a suture retaining portion 110, a suture securing portion 140, and a bone insertion portion 180. Assembly 100 is cannulated along a central longitudinal axis 102 to allow for the optional use of a guide wire through assembly 100 to assist in inserting assembly 100 into bone.

Suture retaining portion 110 includes a generally hollow body 112 having a proximal portion 114, a distal portion 116, and an intermediate portion 118, between the proximal portion 114 and the distal portion 116. Proximal portion 114 includes a cavity 119 having internal threads 120 that are sized to mate with external threads 142 on suture securing portion 140.

Distal portion 116 includes a plurality of distally extending fingers 122 that are separated from adjacent fingers 122 by a longitudinal gap 124. Fingers 122 form an internal space 125 in distal portion 116. In an exemplary embodiment, four fingers 122 are provided, although those skilled in the art will recognize that more or less than four fingers 122 can be provided. A distal end of each finger 122 includes an internal lip 126 that is used to engage bone insertion portion 180. Internal space 125 has an internally extending radial lip 128 that narrows internal space 125 in a proximal direction.

Intermediate portion 118 includes a plurality of suture openings 130 formed therein. In an exemplary embodiment, suture openings 130 include a first suture opening 130a and a second suture opening 130b that are diametrically opposed from each other.

Suture securing portion 140 comprises a set screw that is insertable into cavity 119 and is movable between a first position, shown in FIG. 2, wherein a suture 50 is moveable within the suture retaining portion and a second position, shown in FIG. 3, wherein the suture 50 is frictionally secured within suture retaining portion 110.

Bone insertion portion 180 includes a distal bone insertion end 182 that is adapted for insertion into a bone. Distal bone insertion end 182 includes a threaded portion 184 for gripping the bone.

Bone insertion portion 180 also includes a proximal bone insertion end 186 connected to suture retaining portion 110. Proximal bone insertion end 186 includes a radially extending lip 188 that is used to retain suture retaining portion 110. A hex head 190 is located proximally of lip 188 and is used to insert bone insertion portion 180 into a bone.

To insert assembly 100, bone insertion portion 180 is threaded sub-flush into bone, either using a guide wire (not shown) or, alternatively, without a guide wire. A suture 50 is inserted into first suture opening 130a through suture retaining portion 110 and out second suture opening 130b.

Suture retaining portion 110 is secured onto proximal bone insertion end 186 such that lip 126 on suture retaining portion 110 is forced over lip 188 on bone insertion portion 180 to rotatably secure suture retaining portion 110 onto bone insertion portion 180. Suture 50 can be tensioned by pulling on a free end 58.

Suture securing portion 140 can be screwed down into cavity 119 to frictionally secure suture 50 within suture retaining portion 110.

Figures 5, 6:
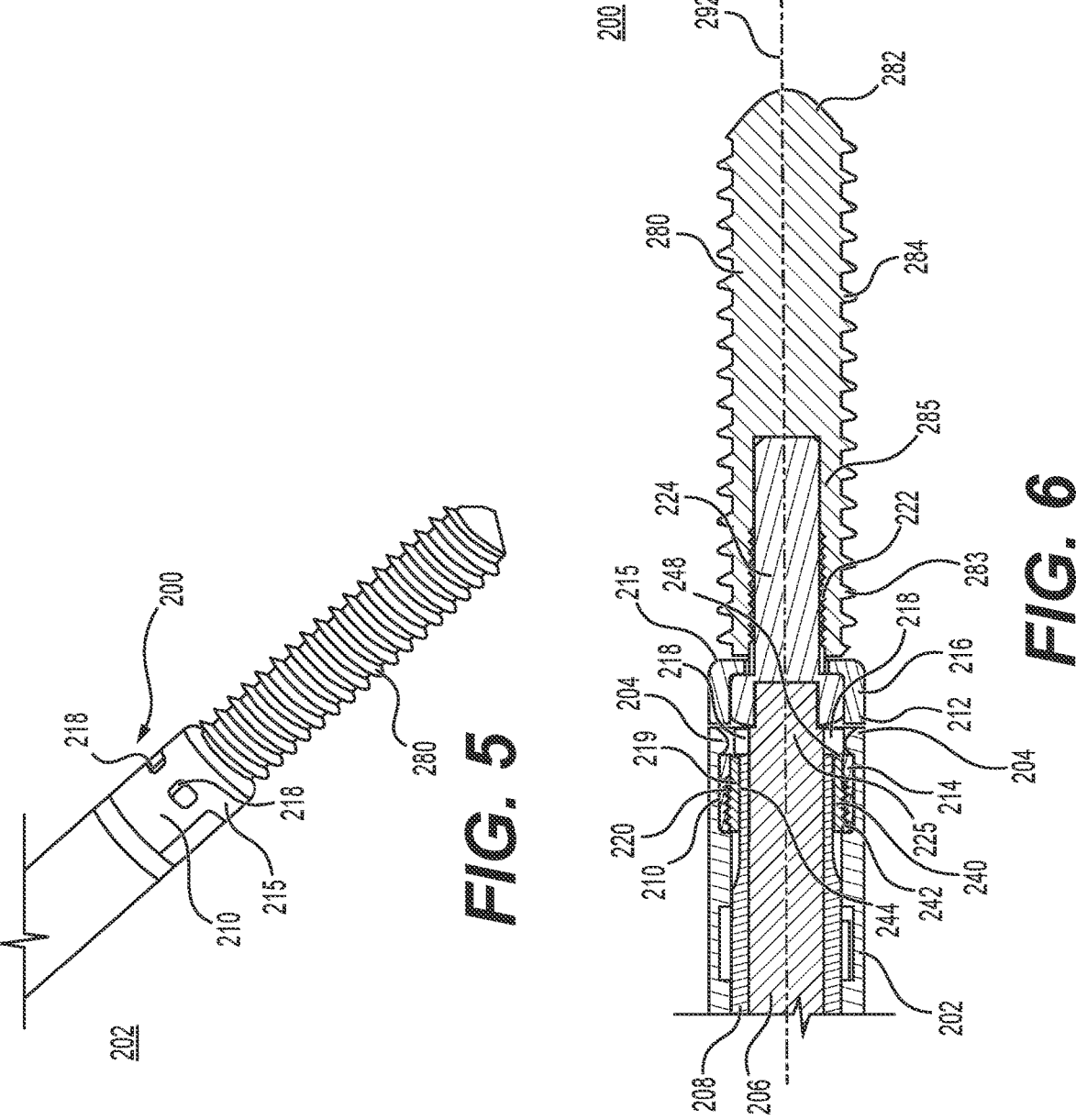
FIG. 5 is a perspective view of a fixation assembly according to an alternative exemplary embodiment.
FIG. 6 is a sectional view of the assembly of FIG. 5 in a suture release position.
Figures 7, 8:
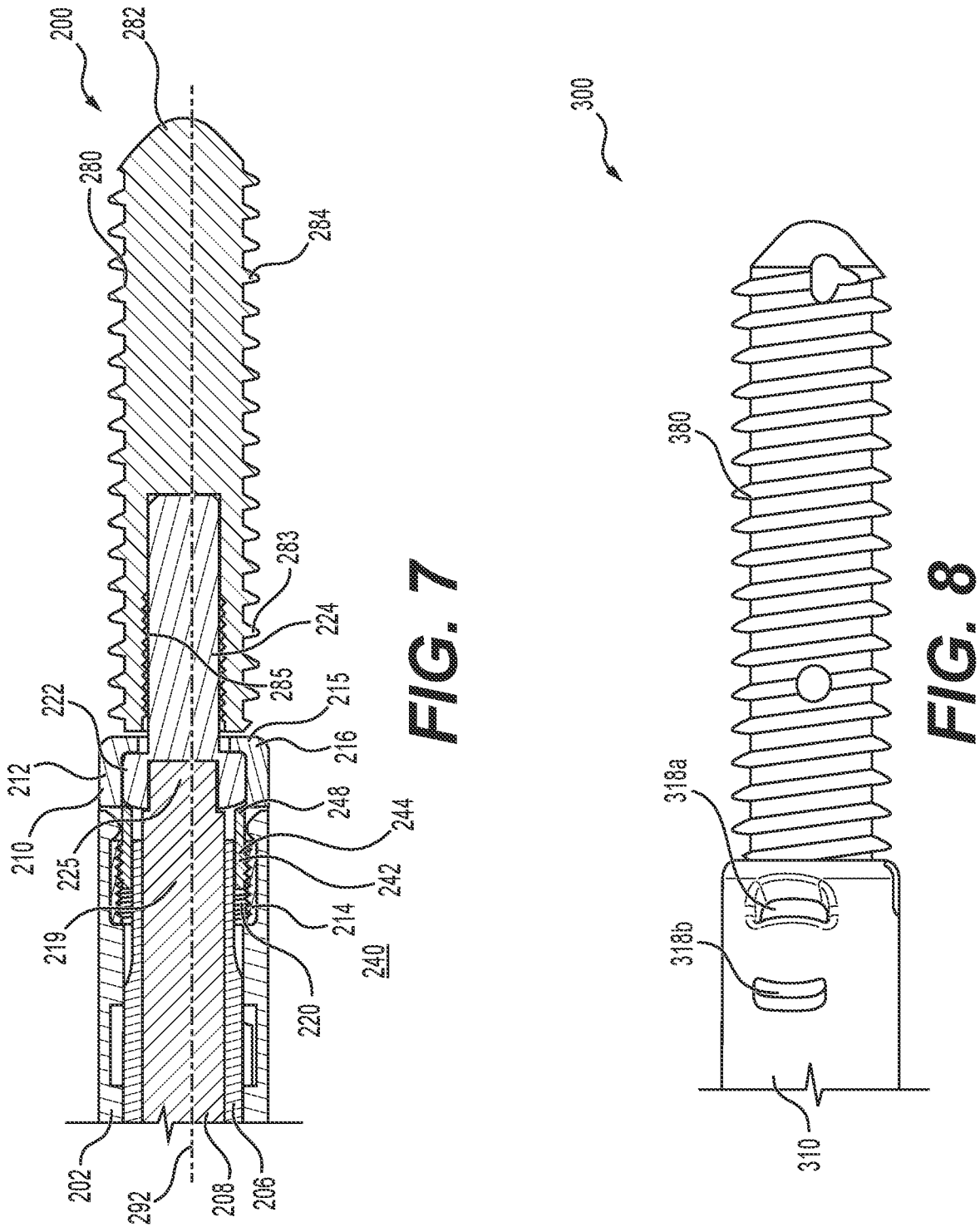
FIG. 7 is a sectional view of the assembly of FIG. 5 in a suture restraining position.
FIG. 8 is a side elevational view of a fixation assembly according to an alternative exemplary embodiment.

Referring to FIGS. 5-7, a syndesmosis fixation assembly 200 ("assembly 200") according to an alternative exemplary embodiment is shown. Assembly 200 includes a suture retaining portion 210, a suture securing portion 240, and a bone insertion portion 280.

Suture retaining portion 210 includes a generally hollow body 212 having a proximal portion 214 and a distal portion 216. Proximal portion 214 includes a cavity 219 having internal threads 220 that are sized to mate with external threads 242 on suture securing portion 240. Proximal portion 214 also includes a plurality of suture openings 218 extending therethrough. Proximal portion 214 also includes a cap 215.

Distal portion 216 includes a head 222 having a circular outer perimeter 223 and a threaded body 224 having a narrower cross section than head 222. Head 222 has a cavity 225 adapted to receive an insertion tool 206 to rotate head 222. In an exemplary embodiment, cavity 225 accepts a hex head driver. Head 222 is sized to fit within cap 215 so that head 222 rotatably engages cap 215. Threaded body 224 is sized to internally thread into a proximal threaded cavity 285 in a proximal bone insertion end 283 of bone insertion portion 280.

Suture securing portion 240 comprises a set screw 242 that is insertable into cavity 219 and is movable between a first position, shown in FIG. 6, wherein a suture is moveable within suture retaining portion 210 and a second position, shown in FIG. 7, wherein the suture can be frictionally secured within suture retaining portion 110. Set screw 242 is generally hollow with an internal hex face 244 and a distal end 248.

Bone insertion portion 280 includes a distal bone insertion end 282 that is adapted for insertion into a bone. Distal bone insertion end 282 includes a threaded portion 284 for gripping the bone. A central longitudinal axis 292 extends between distal bone insertion end 282 and proximal bone insertion end 283.

Suture securing portion 240 is threadingly disposed in cavity 219 and movable between a first position wherein the suture is moveable within suture retaining portion 210 and a second position wherein the suture is frictionally secured within suture retaining portion 210. The first position is a distal position relative to bone insertion portion 280 and the second position is a proximal position relative to the bone insertion portion 280.

To insert assembly 200, head 222 is inserted through cap 215 such that threaded body 224 extends distally from cap 215. A suture (not shown) in inserted into one suture opening 218 and out another suture opening 218. A retaining tool 202 is inserted over suture retaining portion so that nubs 204 on distal ends of retaining tool 202 are inserted into diametrically opposing suture openings 218 and help to prevent rotation of cap 215 and the suture as assembly 200 is driven into the bone.

Next, threaded body 215 is inserted into threaded cavity 285 in proximal bone insertion end 283 of bone insertion portion 280 and bone insertion portion 280 is driven into a bone using a driver 206 inserted into head 222. Then, an outer driver 208 is used to rotate set screw 242 distally from the position shown in FIG. 6 to the position shown in FIG. 7 until distal end 248 of set screw 242 engages the top of head 222, thereby securing the suture between set screw 242 and head 222.

Figures 9, 10:
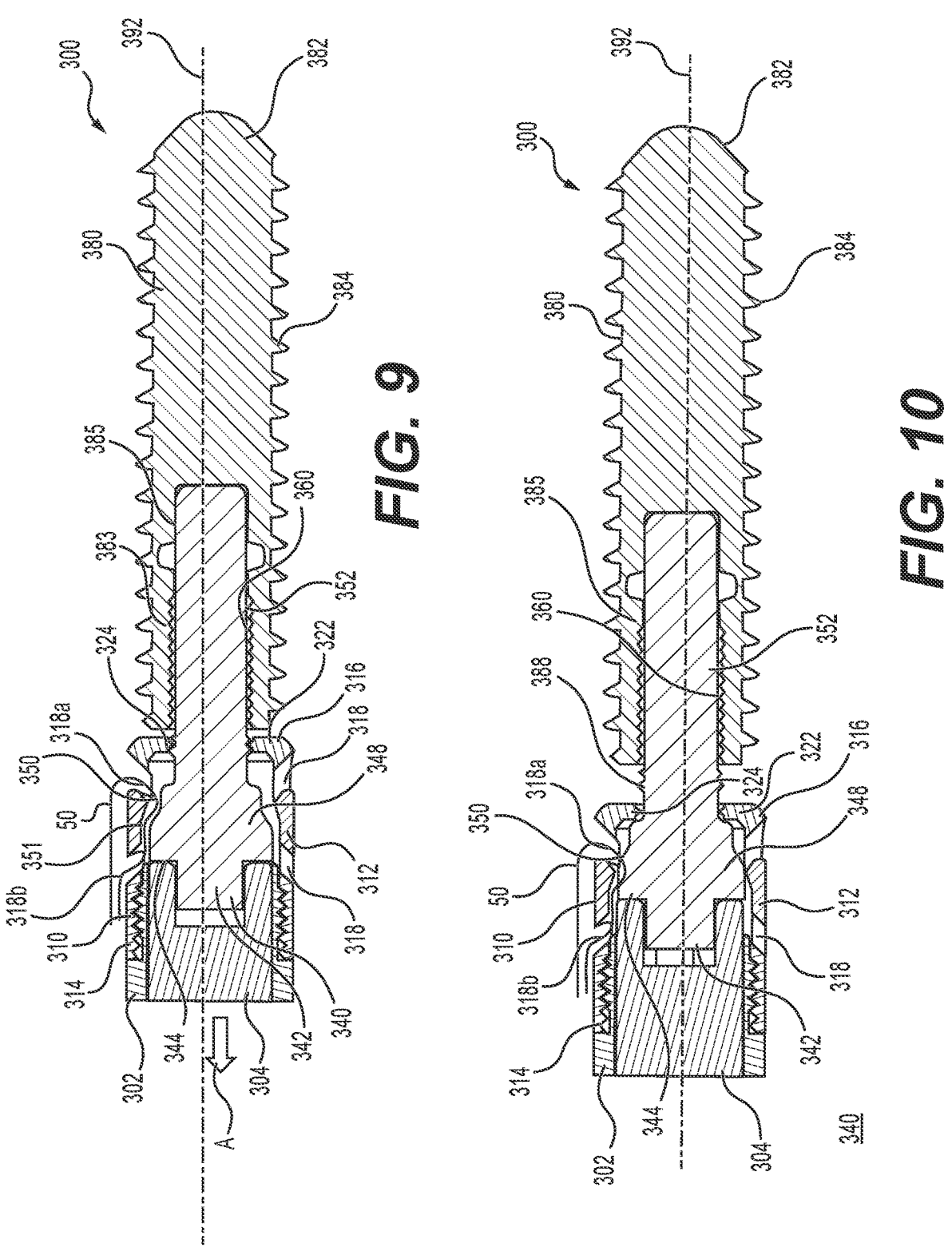
FIG. 9 is a sectional view of the assembly of FIG. 8 in a suture release position.
FIG. 10 is a sectional view of the assembly of FIG. 8 in a suture restraining position.

Referring to FIGS. 8-10, a syndesmosis fixation assembly 300 ("assembly 300") according to an alternative exemplary embodiment is shown. Assembly 300 includes a suture retaining portion 310, a suture securing portion 340, and a bone insertion portion 380.

Suture retaining portion 310 includes a generally hollow body 312 having a proximal portion 314 and a distal portion 316. Proximal portion 314 includes internal threads 317 that accepts an insertion tool 302. Proximal portion 314 also includes a plurality of suture openings 318 extending therethrough. The plurality of suture openings 318 comprises a first opening 318a and a second opening 318b, proximal of first opening 318a.

Distal portion 316 includes a cap 322 that is sized to receive suture securing portion 340 to frictionally engage a suture 50 that extends from suture openings 318a, 318b. A lip 324 extends radially inwardly from cap 322.

Suture securing portion 340 comprises a head 342 adapted to receive an insertion tool 304 to rotate head 342. In an exemplary embodiment, head 342 accepts a hex head driver. Head 342 ends in an annular shoulder 344 that engages insertion tool 304. Head 342 includes a bulbous body 348 extending distal of shoulder 344, with a circumferential groove 350 formed therein. A passage 351 is provided between body 348 and suture retaining portion 310 from first suture slot 318a to second suture slot 318b so that suture 50 can be slid along passage 351.

A distal end 352 of suture securing portion 340 includes a threaded body 360 that is sized to internally thread into a proximal threaded cavity 385 in a proximal bone insertion end 383 of bone insertion portion 380. A lip 388 extends around distal end 352 between threaded body 360 and head 342.

Bone insertion portion 380 includes a distal bone insertion end 382 that is adapted for insertion into a bone. Distal bone insertion end 382 includes a threaded portion 384 for gripping the bone. A central longitudinal axis 392 extends between distal bone insertion end 382 and proximal bone insertion end 383.

Suture securing portion 340 is disposed in suture retaining portion 310 such that and movable between a first position wherein suture 50 is moveable within suture retaining portion 310 and a second position wherein suture 50 is frictionally secured suture retaining portion 310 and suture securing portion 340. The first position is a distal position relative to bone insertion portion 380 and the second position is a proximal position relative to the bone insertion portion 380.

Referring to FIGS. 9 and 10, to insert assembly 300, threaded body 360 of suture securing portion 340 is inserted through cap 322 such that threaded body 360 extends distally from cap 322 so that lip 324 is distal of lip 388. A suture 50 in inserted into one suture opening 218*a* and out another suture opening 218*b*.

A first retaining tool 302 is threaded onto internal threads 317 of proximal portion 314 to prevent rotation of suture retaining portion 310. A second retaining tool 304 is inserted into first retaining tool 302 and over head 342 until second training tool engages shoulder 344.

Next, threaded body 360 is inserted into threaded cavity 385 in proximal bone insertion end 383 of bone insertion portion 380 and bone insertion portion 380 is driven into a bone using a driver 304 inserted over head 342 until bone insertion portion is sub-flush with bone. Both drivers 302, 304 can then be removed.

To frictionally secure suture 50, cap 322 is pulled proximally in the direction of arrow "A" in FIG. 9 so that lip 324 snaps over lip 388 and remains proximally over lip 388. Suture retaining portion 310 engages head 342 so that passage 351 is reduced, thereby frictionally securing suture 50 between body 348 of head 342 and suture retaining portion 310.

Referring to FIGS. 11-14, a syndesmosis fixation assembly 400 ("assembly 400") according to an alternative exemplary embodiment is shown. Assembly 400 includes a suture retaining portion 410, a suture securing portion 420, and a bone insertion portion 440.

Suture retaining portion 410 includes a plurality of distally extending fingers 412 that are separated from adjacent fingers 412 by a longitudinal gap 414. Fingers 412 form an internal space 415 in suture retaining portion 410. In an exemplary embodiment, four fingers 412 are provided, although those skilled in the art will recognize that more or less than four fingers 412 can be provided.

Internal space 415 has an internal thread 416 to threadingly accept and engage suture securing portion 420. Internal space 415 bottoms out on a landing 417. Suture retaining portion 410 also includes external ribbing 418 that allows assembly 400 to be inserted into a pre-drilled hole (not shown) but resists being pulled out.

Suture securing portion 420 includes a deformable spring anchor 422 that serves as both suture securing portion 420 as well as an anchor to secure assembly 400 in bone. Spring anchor 422 includes a body portion 424 with a plurality of anchor legs 426 extending outwardly therefrom. The number of anchor legs 426 is the same number as the number of longitudinal gaps 414 such that each anchor leg 424 extends into a respective gap 414, while body portion 424 can slide within internal space 415.

Suture securing portion 420 further includes a set screw 428 that is insertable into internal space 415. Set screw 428 has a blunt distal tip 430 and a proximal head 432 that is configured to accept a driver (not shown) for rotating set screw 428 distally into internal space 415. Set screw 428 has an external thread 434 that mates with internal thread 416 to advance set screw 428 distally.

Bone insertion portion 440 extends distally from suture retaining portion 410 and includes a blunt distal tip 442 and external ribbing 444 that is an extension of the external ribbing 418 on suture retaining portion 410.

Figures 11, 12, 13, 14:
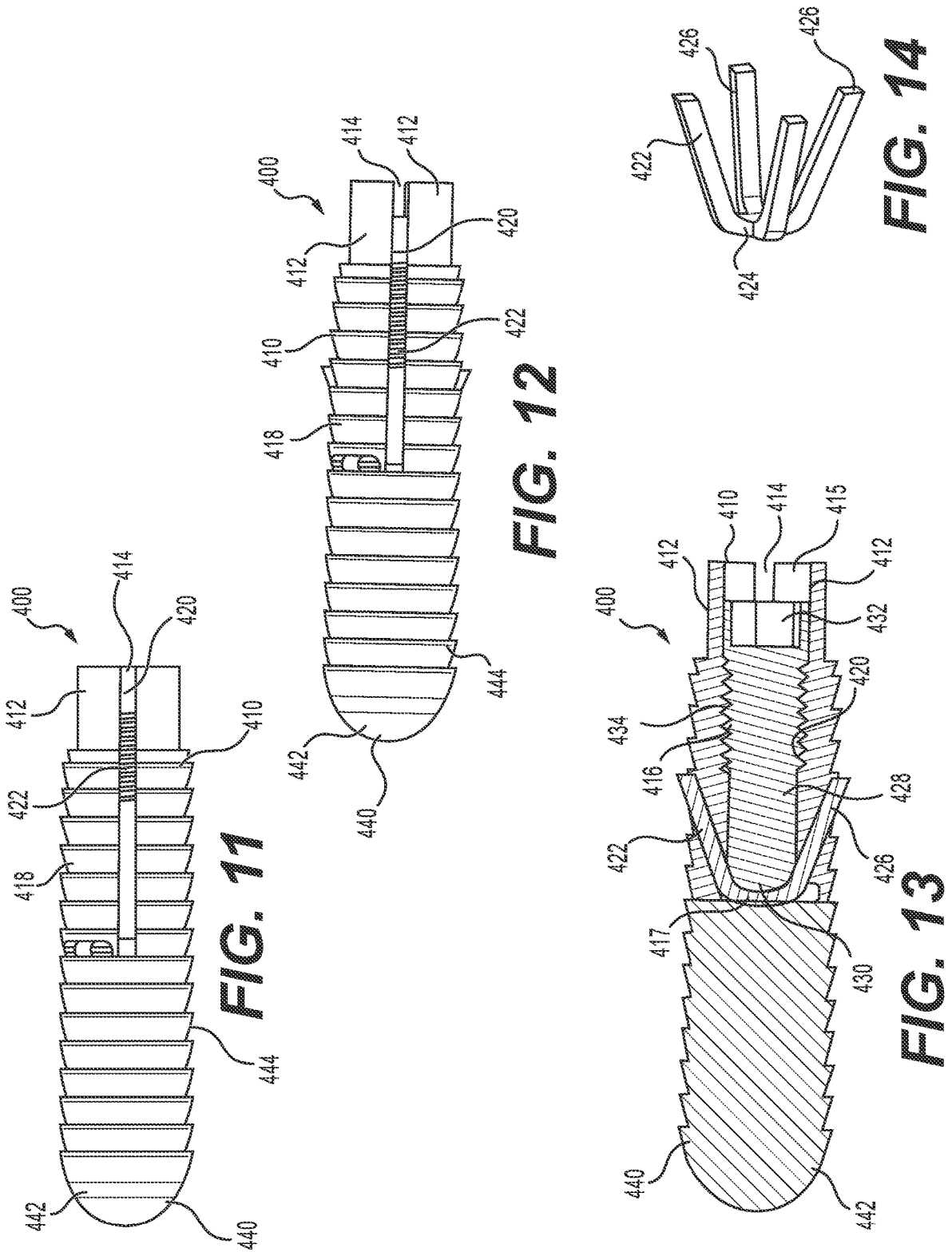
FIG. 11 is a side elevational view of a fixation assembly according to an alternative exemplary embodiment.
FIG. 12 is a side elevational view of the assembly of FIG. 11 with anchor legs in a deployed position.
FIG. 13 is a sectional view of the assembly of FIG. 11 with the anchor legs in the deployed position.
FIG. 14 is a perspective view of the anchor used with the assembly of FIG. 11.

In an insertion condition, anchor legs 426 are stored within the perimeter of fingers 412, as shown in FIG. 11. A suture (not shown) can be inserted into suture retaining portion 410 such that each end of the suture extends outwardly of one of gaps 414. Bone securing portion 440 is inserted into the bone and set screw 428 is advanced distally into internal space 415, driving anchor 422 distally until anchor 422 frictionally engages the suture between anchor body portion 424 and landing 417 of internal space 415.

As set screw 428 is further advanced distally, anchor legs 426 are deformed to splay outwardly from the stored position, as shown in FIG. 11, to a deployed position, as shown in FIGS. 12 and 13.

Referring to FIGS. 15-18, a syndesmosis fixation assembly 450 ("assembly 450") according to an alternative exemplary embodiment is shown. Assembly 450 includes a suture retaining portion 460, a suture securing portion 470, and a bone insertion portion 490.

Suture retaining portion 460 includes a plurality of distally extending generally semi-circular leg portions 462 that are separated from each other by a pair of diametrically opposed longitudinal gaps 464. Leg portions 462 form an internal space 465 in suture retaining portion 460. In an exemplary embodiment, two diametrically opposed leg portions 462 are provided, although those skilled in the art will recognize that more or less than two leg portions 462 can be provided.

Internal space 465 has an internal thread 466 to threadingly accept and engage suture securing portion 470. Internal space 465 bottoms out on a landing 467. A pair of diametrically opposed suture slots 468 extend from internal space 465 through each leg portion 462. Suture slots 468 are generally rectangular in cross section and are sized to allow a suture (not shown) to extend therethrough. Suture retaining portion 460 also includes external ribbing 469 that allows assembly 450 to be inserted into a pre-drilled hole (not shown) but resists being pulled out.

Suture securing portion 470 includes a pair of diametrically opposed cam-operated blades 476 that form an anchor to secure assembly 450 in bone. Blades 476 are movable between a stored position in which blades 476 are stored wholly within gaps 464, as shown in FIG. 15, and a deployed position in which blades 476 extend outwardly of leg portions 462, as shown in FIGS. 16-18.

Each blade 476 includes a sloped cam face 478 that, in a stored position, extends obliquely relative to a longitudinal axis 480 of suture retaining portion 460. A distal end 482 of each blade 476 is pivotally attached to bone insertion portion 490 at a pivot 484, located distal of landing 467.

Suture securing portion 470 includes a set screw 479 that is insertable into internal space 465. Set screw 479 has a blunt distal tip 480 and a proximal head 482 that is configured to accept a driver (not shown) for rotating set screw 479 distally into internal space 465. Set screw 479 has an external thread 484 that mate with internal thread 466 to advance set screw 479 distally.

Bone insertion portion 490 extends distally from suture retaining portion 460 and includes a blunt distal tip 492 and external ribbing 494 that is an extension of the external ribbing 468 on suture retaining portion 460.

In an insertion condition, blades 476 are stored within the perimeter of leg portions 462. A suture (not shown) can be inserted into suture retaining portion 460 such that each end of the suture extends outwardly of one of suture slots 468. Bone insertion portion 490 is inserted into the bone and set screw 479 is advanced distally into internal space 465, engaging cam face 478 of each blade 476 and pushing blades 476 outwardly through their respective gap 464 to secure assembly 450 into bone. As set screw 479 is further advanced distally, set screw 479 engages the suture and frictionally secures the suture between distal tip 480 and landing 467.

Figure 19:
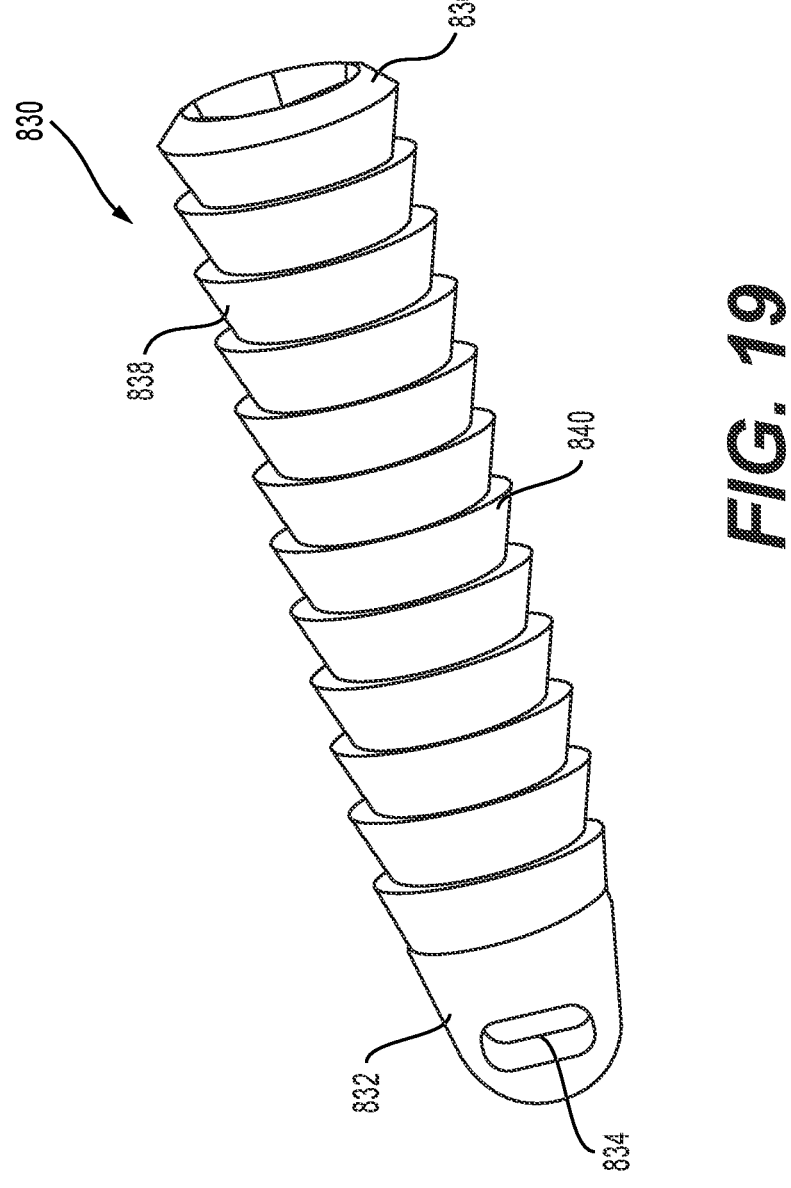
FIG. 19 is a perspective view of a fixation device according to an alternative exemplary embodiment.

Alternatively, as shown in FIG. 19, an anchor 830 includes a distal tip 832 with a transverse passage 834 passing through. Anchor 830 also has a proximal end 836 configured to accept a driver (not shown). A body 838 having uni-directional ribbing 840 extends from proximal end 836 to distal tip 832.

To insert anchor 830, suture 50 or suture tape 52 (not shown) is passed through transverse passage 834 and anchor is tapped into a pre-drilled hole on tibia 40 (not shown). Suture 50 or suture tape 52 is wedged between anchor 830 and the wall of hole.

Figures 20, 21:
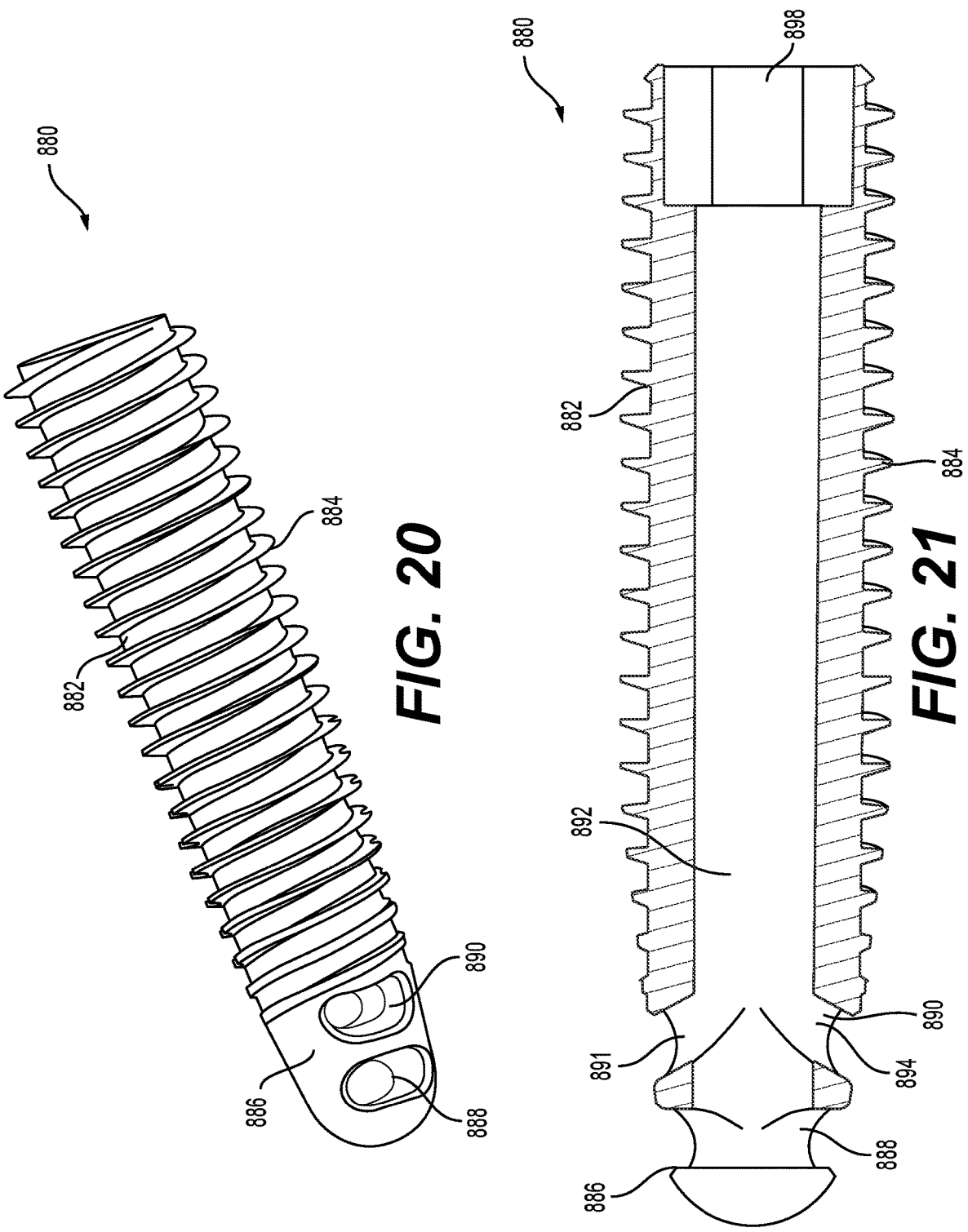
FIG. 20 is a perspective view of a fixation device according to another alternative exemplary embodiment.
FIG. 21 is a sectional view of the device of FIG. 20.

In an alternative embodiment shown in FIGS. 20 and 21, an anchor 880 includes a cannulated body 882 having an external thread 884. A distal tip 886 includes a transverse, first passage 888 and an oblique, second passage 890 proximal of first passage 888. Second passage 890 includes a first portion 891 that extends obliquely upwardly into an internal cannula 892 and a second portion 894, diametrically opposite from first portion 891, that also extends obliquely upwardly into internal cannula 892. Internal cannula 892 extends from first passage 888 to a proximal end 896 that can include a hex head 898 to accommodate a driver (not shown). The driver can be cannulated to allow a suture to extend therethrough.

Suture 50 or suture tape 52 is looped through either first passage 888 or second passage 890 and passes through cannula 892 to proximal end 896.

Figure 22:
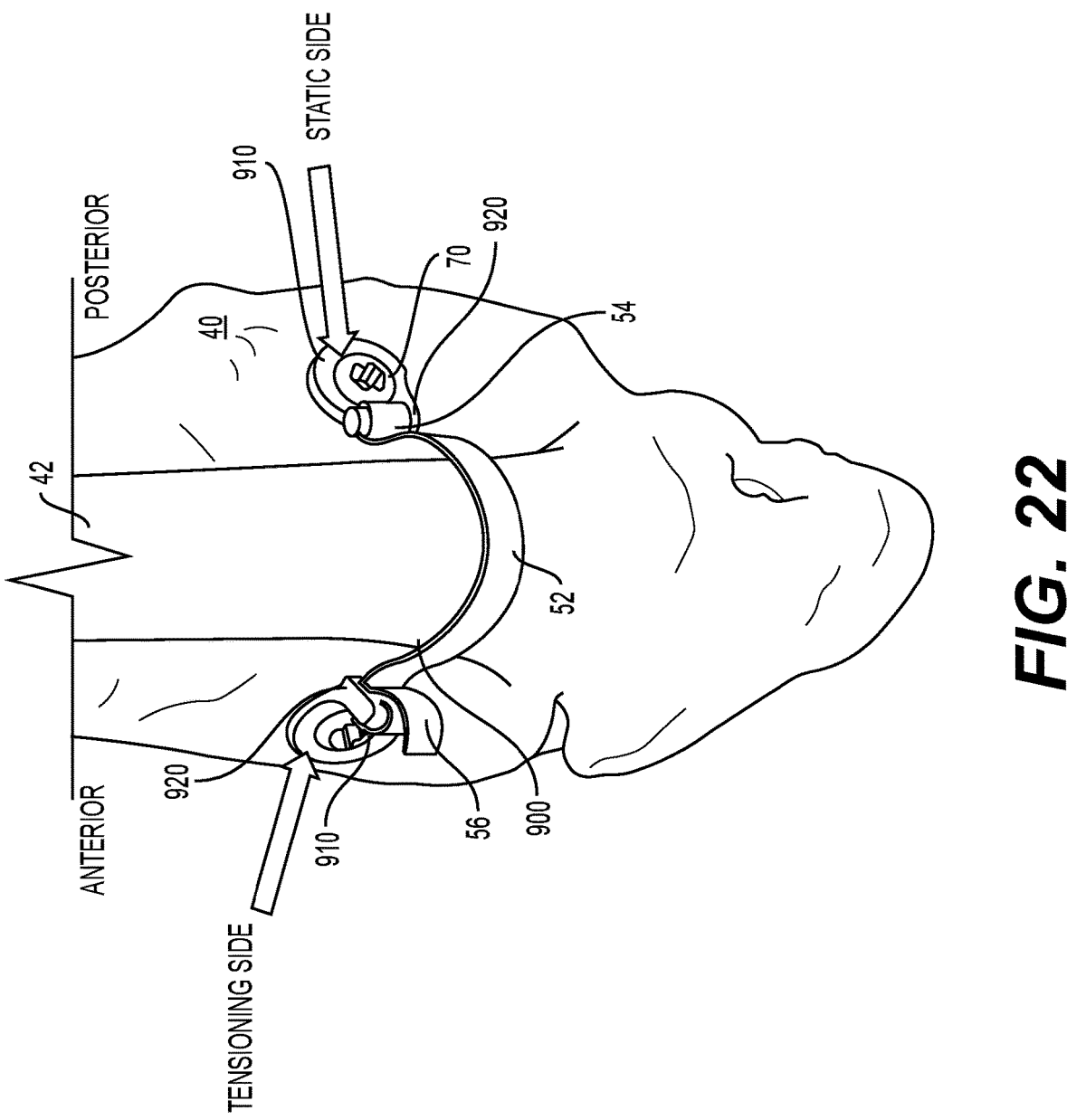
FIG. 22 is a perspective view of a pair of fixation assemblies according to an alternative exemplary embodiment embedded in a tibia and used to reduce a syndesmosis.

An alternative embodiment of an assembly 900 is shown in FIGS. 22-24. Assembly 900 includes a washer 910 and a buckle 920 extending outwardly from washer 910. A suture tape 52 is secured to buckle 920.

Washer 910 includes a generally annular body 912 having a flat top surface 914 and a tapered inner diameter 916. A circular opening 918 is formed within inner diameter 916 and is sized to allow a fixation screw to be inserted therethrough.

Buckle 920 extends at an upward oblique angle from top surface 914 and includes parallel side walls 922, 924, a top connecting member 926, and a central connecting member 928 that each span and connect sides 922, 924 to each other. A first, lower gap 930 is formed between central connecting member 928 and body 912, while a second, upper gap 934 is formed between central connecting member 928 and top member 926.

Referring to FIGS. 22 and 24, to use assembly 900, two screws 70 with washers 910 are inserted into tibia 40 so that suture tape 52 can be wrapped around fibula 42. A first end 54 of suture tape 52 is secured to a first buckle 920. A second end 56 of suture tape 52 stretched over fibula 42 and is inserted through lower gap 930 distal from washer 910 toward washer 910. Second end 56 is then extended upwardly and over top connecting member 926 and then inserted through upper gap 934 distal from washer 910 toward washer 910. Second end 56 is then inserted through lower gap 932, proximate to washer 910 away from washer 910. Second end 56 is then pulled upwardly, tightening suture tape 52 against fibula 42.

Alternatively, second end 56 can be inserted through gaps 932, 934 prior to securing washer 910 to tibia 40, then securing washer 910 to tibia 40, and then tightening suture tape 52 around fibula.

Figure 25:
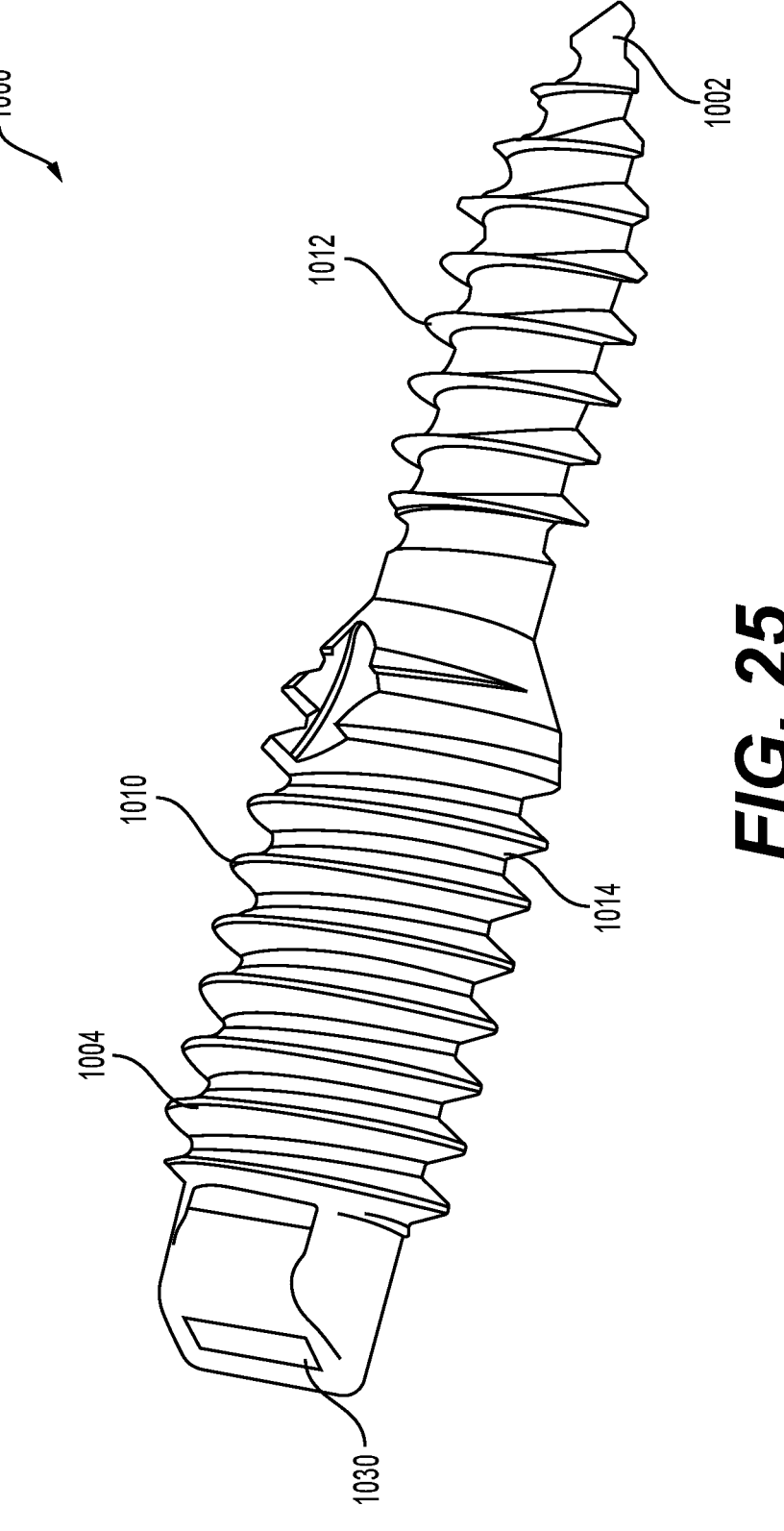
FIG. 25 is a perspective view of a fixation device according to an alternative embodiment.

An alternative embodiment includes a screw 1000 shown in FIG. 25. Screw 1000 has a distal tip 1002 and a proximal end 1004. A threaded body 1010 can extend between tip 1002 and proximal end 1004. Body 1010 can have varying outer diameters along the length of body, such as a narrow body portion 1012 toward distal tip 1002 and a wider body portion 1014 toward proximal end 1004.

Proximal end 1004 includes a buckle 1030 similar to buckle 920 described above with respect to assembly 900. This washerless embodiment allows buckle 1030 to be driven sub-flush of the bone cortex. The tensioning method for suture tape 52 is the same as for assembly 900 described above.

Figures 26, 27:
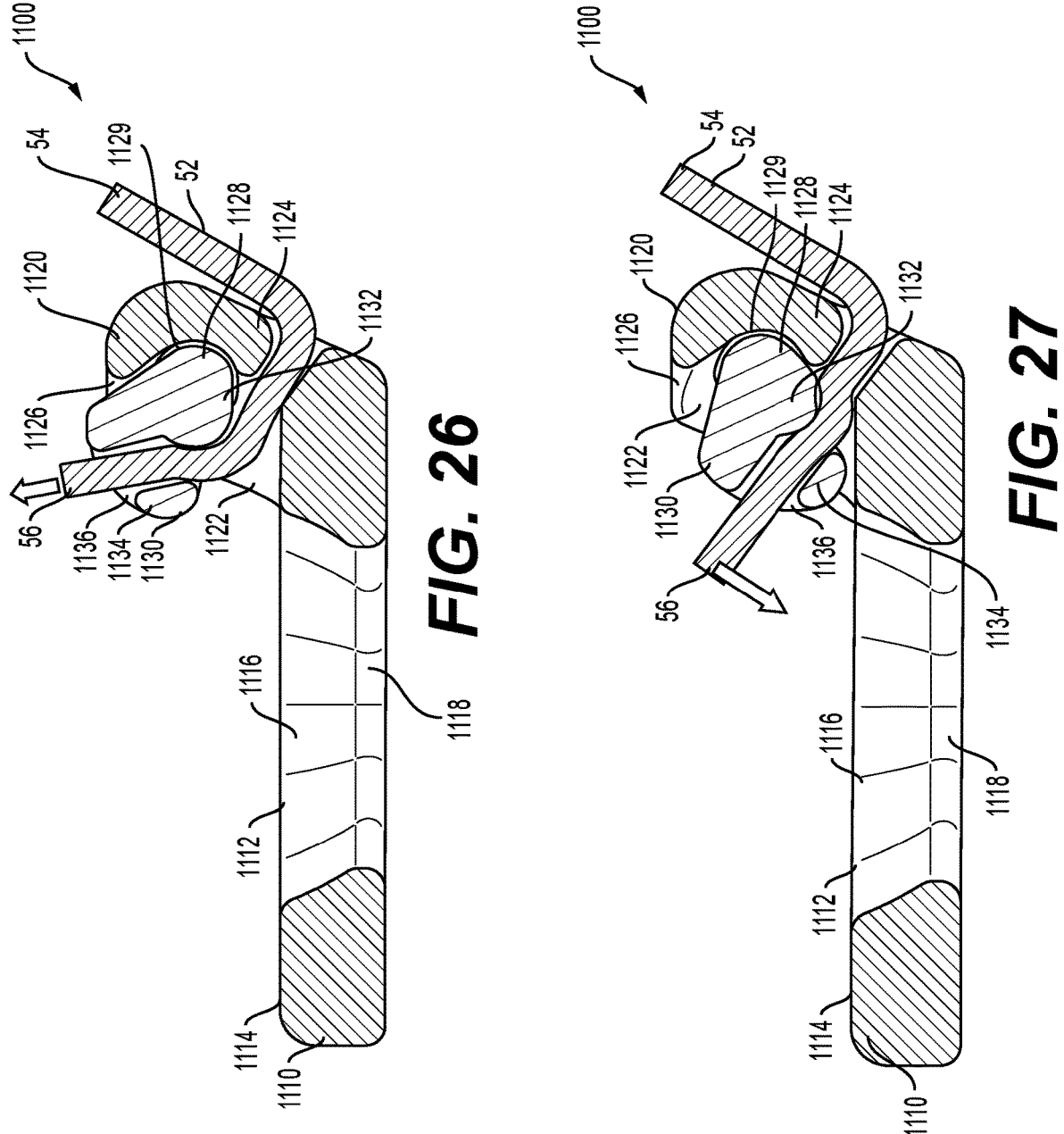
FIG. 26 is a side elevational view, in section, of a washer with a cam operated buckle in a release position according to an alternative exemplary embodiment.
FIG. 27 is a side elevational view, in section, of the washer with am operated buckle of FIG. 26 in a locking position.
Figure 29:
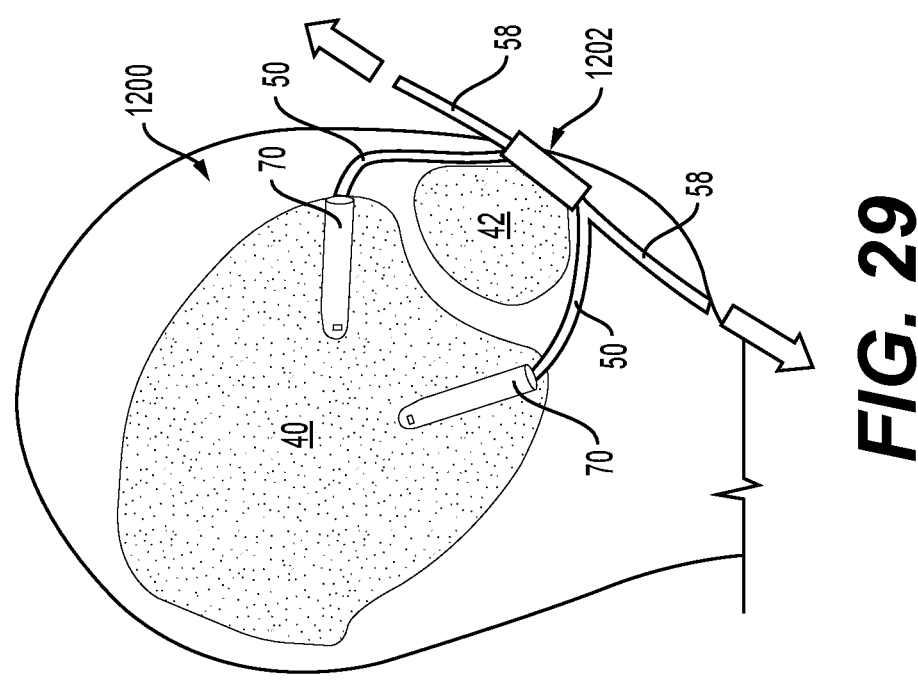
FIG. 29 is a sectional view of the embodiment of FIG. 28 with a clamp connecting two sutures.
Figure 28:
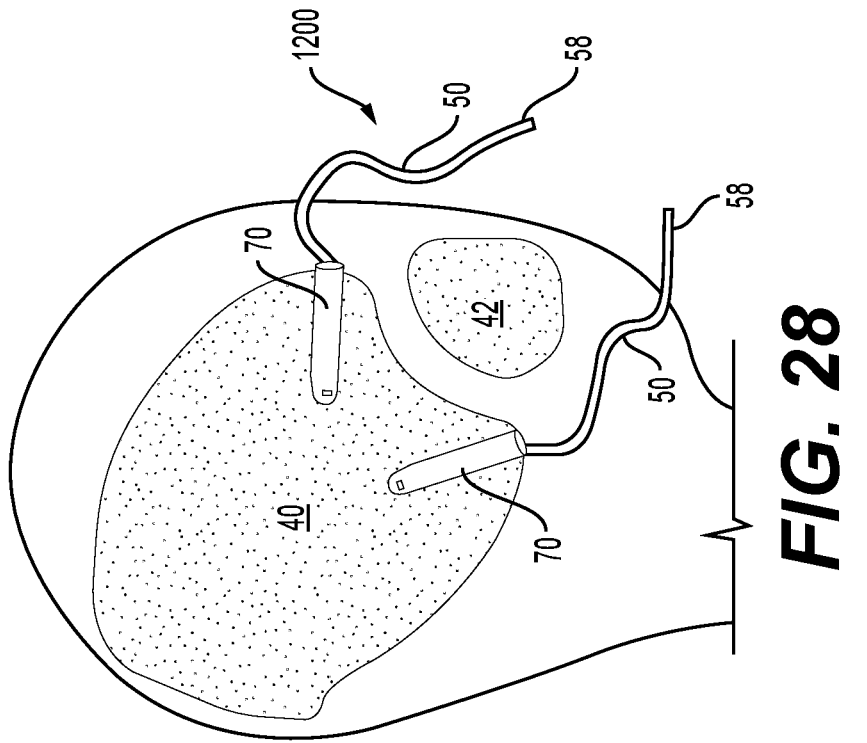
FIG. 28 is a sectional view showing an exemplary method of reducing a syndesmosis according to an alternative exemplary embodiment.

An alternative embodiment of an assembly 1100 is shown in FIGS. 26 and 27. Assembly 1100 includes a washer 1110 with a buckle 1120 that incorporates a cam 1130.

Washer 1110 includes a generally annular body 1112 having a flat top surface 1114 and a tapered inner diameter 1116. A circular opening 1118 is formed within inner diameter 1116 and is sized to allow a fixation screw to be inserted therethrough.

Buckle 1120 extends at an upward oblique angle from top surface 1114 and includes parallel side walls 1122, 1124 and a top connecting member 1126 that spans and connects sides 1122, 1124 to each other. Side walls 1122, 1124 each include a transverse slot 1128. Connecting member 1126 includes a concave inner face 1129.

Each side of cam 1130 includes a pivot portion 1132 that is inserted into transverse slot 1128 to that cam 1130 can pivot about transverse slot 1128. Cam 1130 also includes a lobe 1134 positioned over that is used to bias suture tape 52 against top surface 1112 of washer 1110 and a slot 1136 through which suture tape 52 is inserted.

First end 54 of suture tape 52 can be fixed to another securing device, not shown. Second end 56 of suture tape 52 can be inserted into gap 1127 distal from washer 110 toward washer 1110 and under lobe 1134. Second end 56 is then inserted through slot 1136 in cam 1130. To secure suture tape 52, cam 1130 is pivoted along concave inner face 1129 from the position shown in FIG. 26 to the position shown in FIG. 27. Lobe 1134 is rotated to pinch suture tape 52 down on top surface 114, securing suture tape 52 to assembly 1110.

While assembly 1100 is shown using washer 1110, those skilled in the art will recognize that buckle 1120 with cam 1130 can be used on other securing devices, such as, for example, on screw 1000.

An alternative embodiment of an assembly 1200 is shown in FIGS. 28-32. Assembly 1200 includes screws 70 that are implanted into tibia 40 on either side of fibula 42. A suture 50 is attached to each screw 70 so that each suture 50 has a free end 58. Free ends 58 are drawn over fibula 42 and clamped together, such as by staple 1202. Staple 1202 can be clamped around free ends 58 by a clamping instrument 1210.

Clamping instrument 1210 includes a pair of arms 1212, 1214 that are pivotally attached to each other at a pivot 1216. Instrument 1210 includes a staple receiver 1215 on an opposing side of pivot 1216. Clamping teeth 1218, 1220 are attached to distal ends of arms 1212, 1214, respectively on the opposing side of pivot 1216 and on either side of receiver 1215.

Figure 31:
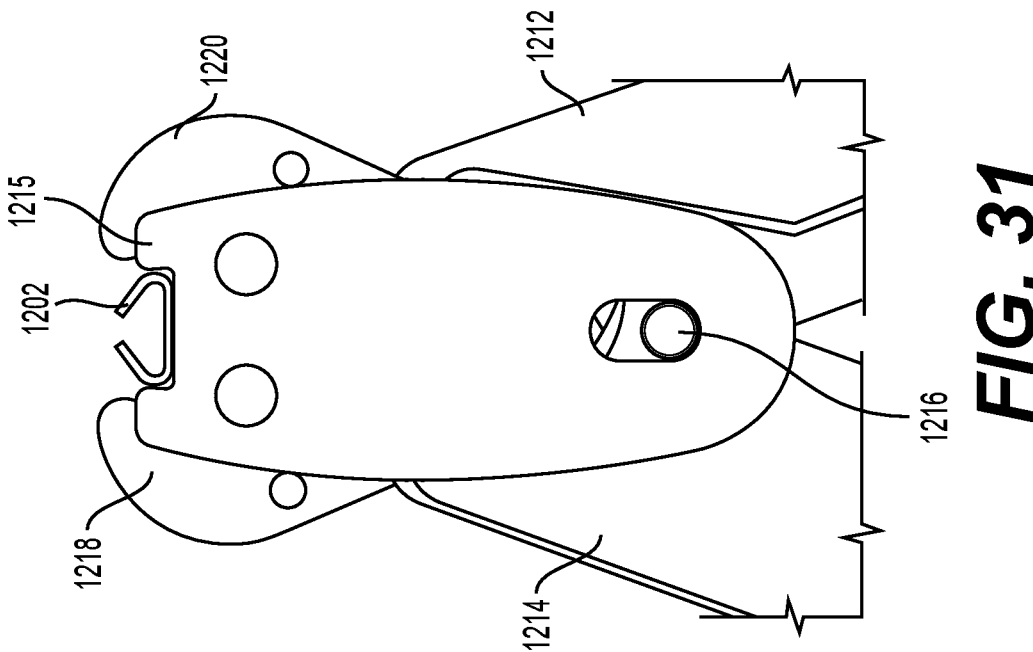
FIG. 31 is a top plan view of a staple inserted into the clamp of FIG. 30.
Figure 30:
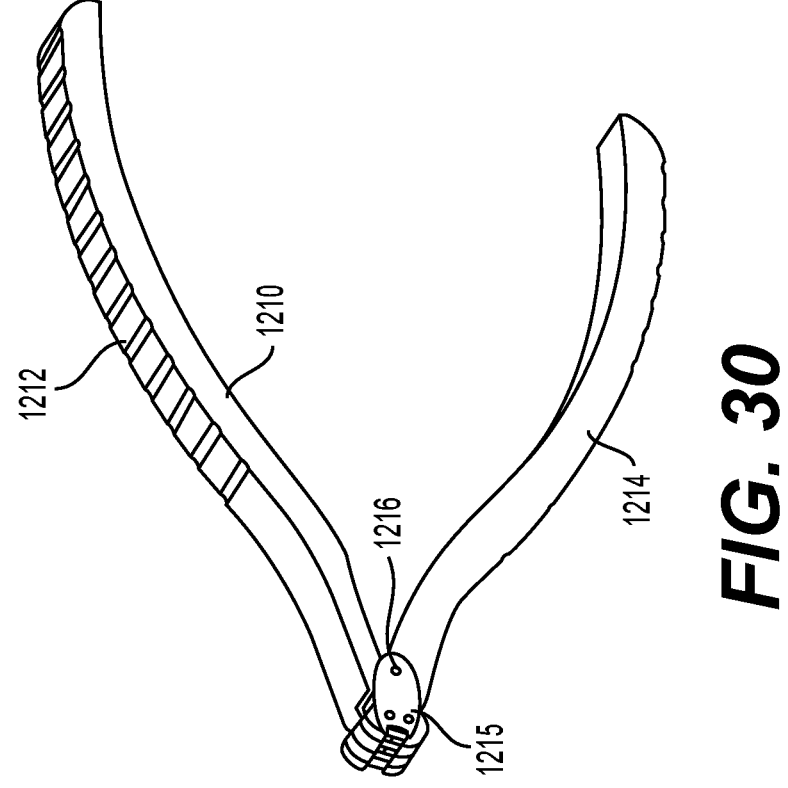
FIG. 30 is a perspective view of an exemplary clamping tool used to clamp the clamp of FIG. 29.
Figure 32:
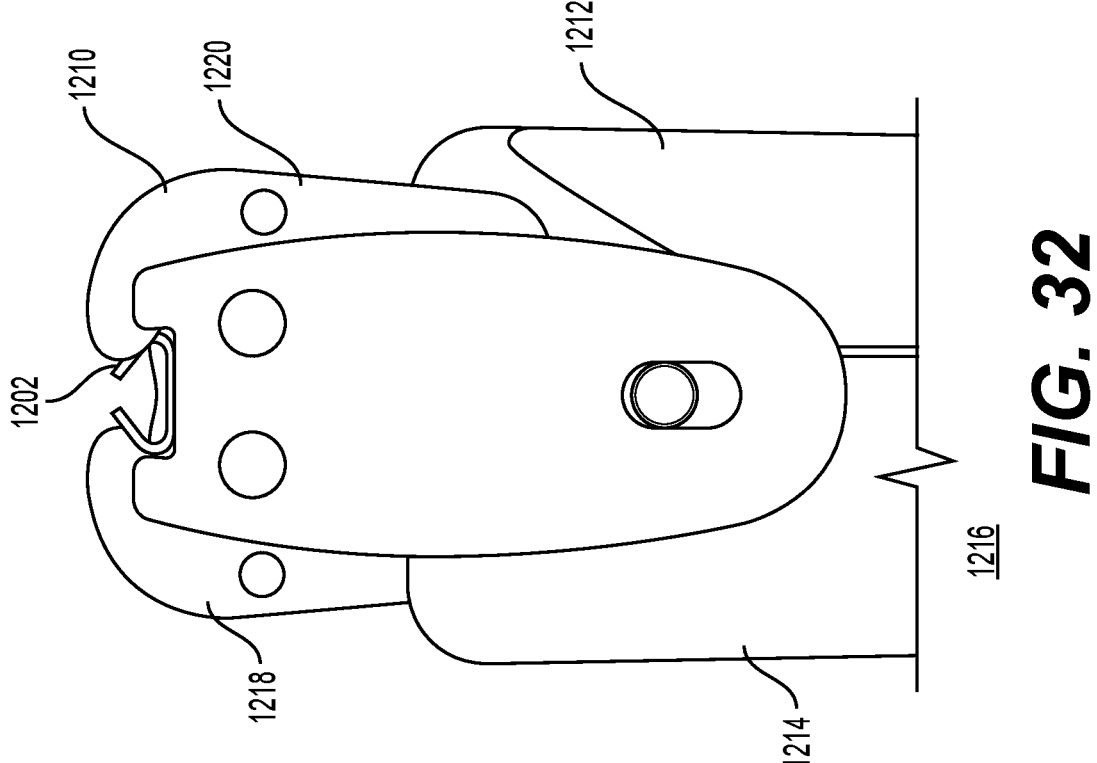
FIG. 32 is a top plan view of the clamp and staple of FIG. 31 having clamped down on the staple.

As shown in FIG. 31, staple 1202 is inserted into receiver 1215. Free ends 58 of sutures 50 are inserted into staple 1202 and arms 1214, 1216 are compressed toward each other as shown in FIG. 32 so that clamping teeth 1218, 1220 close down on staple arms 1204 to clamp free ends 58 of suture 50 within staple.

Figure 33:
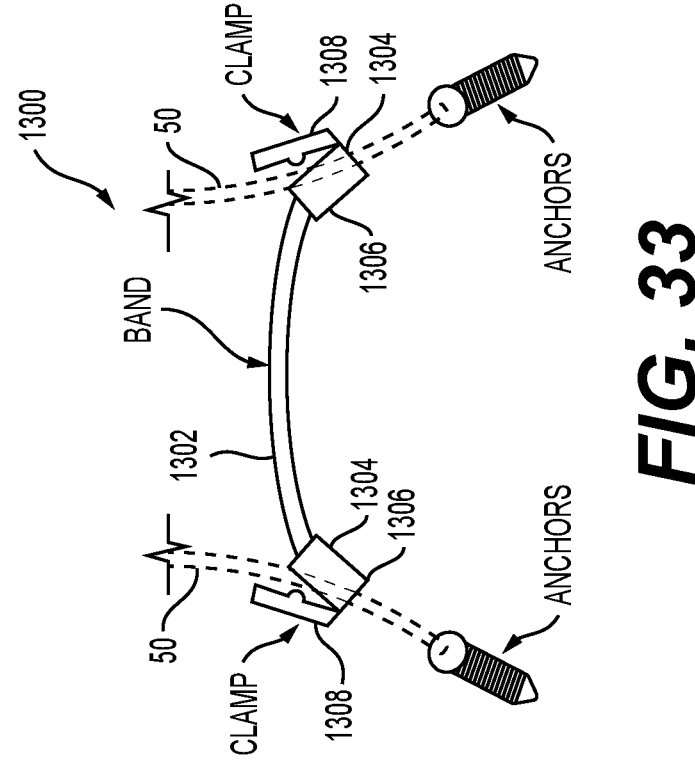
FIG. 33 is a schematic view of a fixation assembly according to an alternative exemplary embodiment.

An alternative embodiment of an assembly 1300 is shown in FIG. 33. Assembly 1300 includes a band 1302 that connects two separate sutures 50 to each other. Sutures 50 can be secured to a bone (not shown) via any of the anchors disclosed herein, such that free ends 58 of sutures extend away from the anchors. Band 1302 includes clamps 1304 are either end thereof to secure free ends 58 of sutures 50.

Each clamp 1304 includes a body 1306 having a closure 1308 pivotally attached thereto. Free end 58 of suture 50 can be inserted through clamp 1304 between body 1306 and closure 1308. Closure 1308 can be pivoted to body 1306 to secure suture 50 between body 1306 and closure 1308.

An advantage to using band 1302 is that band 1302 can be slid along either suture 50 to a select location prior to securing suture 50 to band 1302 in order to avoid engaging any anatomically challenging areas.

The anchors and assemblies disclosed herein can be constructed from biocompatible materials, such as stainless steel, titanium, or other suitable materials or combinations thereof.

It will be further understood that various changes in the details, materials, and arrangements of the parts which have been described and illustrated in order to explain the nature of this device may be made by those skilled in the art without departing from the scope of the device as expressed in the following claims.

The invention claimed is:

1. A syndesmosis fixation assembly comprising:
a suture retaining portion;
a suture securing portion configured to be received in the suture retaining portion, wherein the suture securing portion has an anchor with anchor legs; and
a bone insertion portion having:
a distal bone insertion end adapted for insertion into a bone;
a proximal bone insertion end extending distally from the suture retaining portion;
a central longitudinal axis extending between the distal bone insertion end and the proximal bone insertion end a suture is configured to be inserted into suture retaining portion such that each end of the suture extends outwardly from one of a plurality longitudinal gaps in the suture retaining portion; wherein the suture securing portion further includes a set screw configured to be received into the suture securing portion; and wherein the set screw has threads that mate with internal threads of the suture retaining portion.

2. The syndesmosis fixation assembly of claim 1, wherein the set screw is configured to advance into suture retaining portion to cause the anchor to frictionally engage the suture.

3. The syndesmosis fixation assembly of claim 2, wherein the set screw is configured to splay each anchor leg out of one the longitudinal gaps as set screw is advanced into the suture retaining portion.

4. The syndesmosis fixation assembly of claim 1, wherein the suture retaining portion and the bone insertion portion contain external ribbing.

5. The syndesmosis fixation assembly of claim 1, wherein the anchor is a spring anchor with a body portion and the anchor legs extend outwardly from the body portion.

6. The syndesmosis fixation assembly of claim 1, wherein the set screw has a blunt distal tip.

7. The syndesmosis fixation assembly of claim 6, wherein the distal bone insertion end is blunt.

* * * * *